United States Patent
Fraga-Dubreuil et al.

(10) Patent No.: US 10,143,999 B2
(45) Date of Patent: Dec. 4, 2018

(54) NICKEL HAVING HIGH LIGAND-COMPLEXATION ACTIVITY AND METHODS FOR MAKING THE SAME

(71) Applicant: INVISTA NORTH AMERICA S.A R.L., Wilmington, DE (US)

(72) Inventors: Joan Fraga-Dubreuil, Middlesbrough (GB); Vinay Medhekar, Beaumont, TX (US); John A. Turner, Middlesbrough (GB); Keith Whiston, Darlington (GB)

(73) Assignee: INVISTA NORTH AMERICA S.A R.L., Wilmington, DE (US)

( * ) Notice: Subject to any disclaimer, the term of this patent is extended or adjusted under 35 U.S.C. 154(b) by 0 days.

(21) Appl. No.: 15/525,627

(22) PCT Filed: Nov. 11, 2015

(86) PCT No.: PCT/US2015/060065
§ 371 (c)(1),
(2) Date: May 10, 2017

(87) PCT Pub. No.: WO2016/081230
PCT Pub. Date: May 26, 2016

(65) Prior Publication Data
US 2017/0333879 A1    Nov. 23, 2017

Related U.S. Application Data

(60) Provisional application No. 62/082,431, filed on Nov. 20, 2014.

(51) Int. Cl.
| | |
|---|---|
| *B01J 27/043* | (2006.01) |
| *B01J 23/755* | (2006.01) |
| *B01J 31/18* | (2006.01) |
| *B01J 35/00* | (2006.01) |
| *B01J 35/10* | (2006.01) |

(Continued)

(52) U.S. Cl.
CPC ........... *B01J 23/755* (2013.01); *B01J 31/185* (2013.01); *B01J 31/1845* (2013.01);
(Continued)

(58) Field of Classification Search
CPC .... B01J 23/755; B01J 27/043; B01J 31/1845; B01J 31/185; B01J 35/006
(Continued)

(56) References Cited

U.S. PATENT DOCUMENTS

| | | |
|---|---|---|
| 5,981,722 A | 11/1999 | Chen et al. |
| 7,470,805 B2 | 12/2008 | Rosier et al. |

(Continued)

FOREIGN PATENT DOCUMENTS

| | | |
|---|---|---|
| WO | 2012/170297 A2 | 12/2012 |
| WO | 2012/170300 A2 | 12/2012 |

(Continued)

OTHER PUBLICATIONS

International Search Report and Written Opinion Received for PCT Application No. PCT/US2015/060065, dated Feb. 25, 2016, 12 pages.

(Continued)

*Primary Examiner* — Patricia L. Hailey
(74) *Attorney, Agent, or Firm* — Robert B. Furr, Jr.

(57) ABSTRACT

Disclosed are nickel-containing complexation precursors having high complexation activity for bidentate phosphite ligands. Also disclosed are methods of making the complexation precursors. The disclosed method of generating the nickel-containing complexation precursor includes including contacting a nickel starting material with a reductant under conditions sufficient to generate a nickel-containing complexation precursor having at least about 1,500 ppmw sulfur in the form of sulfide.

19 Claims, 18 Drawing Sheets

(51) Int. Cl.
  *C07F 9/145* (2006.01)
  *C07F 15/04* (2006.01)
(52) U.S. Cl.
  CPC ......... *B01J 35/006* (2013.01); *B01J 35/1009* (2013.01); *C07F 9/145* (2013.01); *C07F 15/04* (2013.01); *B01J 35/002* (2013.01); *B01J 2231/322* (2013.01); *B01J 2531/007* (2013.01); *B01J 2531/847* (2013.01)
(58) Field of Classification Search
  USPC .................................................. 502/222, 337
  See application file for complete search history.

(56) References Cited

U.S. PATENT DOCUMENTS

| | | | |
|---|---|---|---|
| 7,629,484 B2 | 12/2009 | Ritter | |
| 2011/0166376 A1* | 7/2011 | Mastroianni | B01J 31/185 558/338 |
| 2013/0143730 A1* | 6/2013 | Fraga-Dubreuil | B01J 31/1845 502/167 |
| 2013/0345459 A1* | 12/2013 | Ostermaier | C07F 15/04 556/13 |
| 2017/0203287 A1* | 7/2017 | Medhekar | B01J 23/755 |

FOREIGN PATENT DOCUMENTS

| | | |
|---|---|---|
| WO | 2016/004219 A1 | 1/2016 |
| WO | 2016/081230 A1 | 5/2016 |

OTHER PUBLICATIONS

International Preliminary Report on Patentability Report Received for PCT Patent Application No. PCT/US2015/060065, dated May 23, 2017, 9 pages.

* cited by examiner

NICKEL HAVING HIGH LIGAND-COMPLEXATION ACTIVITY AND METHODS FOR MAKING THE SAME

BACKGROUND

Although catalysts that include nickel-ligand complexes are used in many commercially and industrially important chemical processes, procedures for making those catalysts are not optimally efficient. Nickel metal atoms can be combined with phosphorus-containing ligands to generate hydrocyanation catalysts (see, e.g., U.S. Pat. Nos. 5,981,722, 7,629,484, and 7,470,805), but not always with optimal results. Nickel is poorly soluble, and many nickel metal preparations are unsuitable for use in catalysts. For example, when nickel metal is agglomerated, poorly reduced, or impurities are present, low levels of nickel combine with phosphorus-containing ligands and only small amounts of catalyst are formed. Moreover, nickel starting materials from different commercial sources can have different properties, and even when processed identically one source can provide nickel metal that can efficiently form complexes with phosphorus-containing ligands, while another source does not.

Nickel having better complex-forming properties is desirable, as are more efficient processes for making such nickel, so that greater percentages of nickel preparations can be used in nickel-ligand catalysts and so that less waste is generated during catalyst preparation.

SUMMARY OF THE INVENTION

Disclosed is a method of generating nickel-containing complexation precursor. The method includes contacting a nickel starting material with a reductant. The contacting is performed under conditions sufficient to generate a nickel-containing complexation precursor having at least about 1,500 ppmw sulfur in the form of sulfide.

In various embodiments, the present invention provides a nickel-containing complexation precursor that includes at least 1,500 ppmw sulfur in the form of sulfide, such as about 1,500 ppmw to about 500,000 ppmw sulfide. The sulfide can be amorphous nickel sulfide.

In various embodiments, the present invention provides a method for determining the ligand-complexation activity of a nickel-containing complexation precursor. The method includes determining the ligand-complexation activity from the concentration of sulfur as amorphous nickel sulfide in the nickel-containing complexation precursor, wherein a higher concentration of sulfur as amorphous nickel sulfide indicates a higher ligand-complexation activity of the nickel-containing complexation precursor.

Various embodiments of the present invention have certain advantages over other active nickels and methods of making the same. The inventors have discovered a correlation between the presence of sulfur in the form of sulfide in a nickel-containing complexation precursor (e.g., as amorphous nickel sulfide) and ligand-complexation activity of the complexation precursor. Further, the inventors have determined various ways for controlling the concentration of sulfur in the form of sulfide in the nickel-containing complexation precursor. Various embodiments provide the ability to choose suitable sources of sulfur, as well as process conditions, which provide nickel products with a desired chemical composition and therefore desired activities. Various embodiments of the method can produce a nickel metal having a higher ligand-complexation activity than other methods. In some embodiments, by controlling the amount of sulfur in the form of sulfide in the nickel metal produced, the method can more consistently and predictably produce a complexation precursor having a particular activity (e.g., a high activity) of ligand-complexation activity. In various embodiments, the present invention provides a method of determining or predicting the ligand-complexation activity of nickel metal that is more accurate than other methods.

BRIEF DESCRIPTION OF THE FIGURES

The drawings illustrate generally, by way of example, but not by way of limitation, various embodiments discussed in the present document.

DETAILED DESCRIPTION OF THE INVENTION

Figure 1:
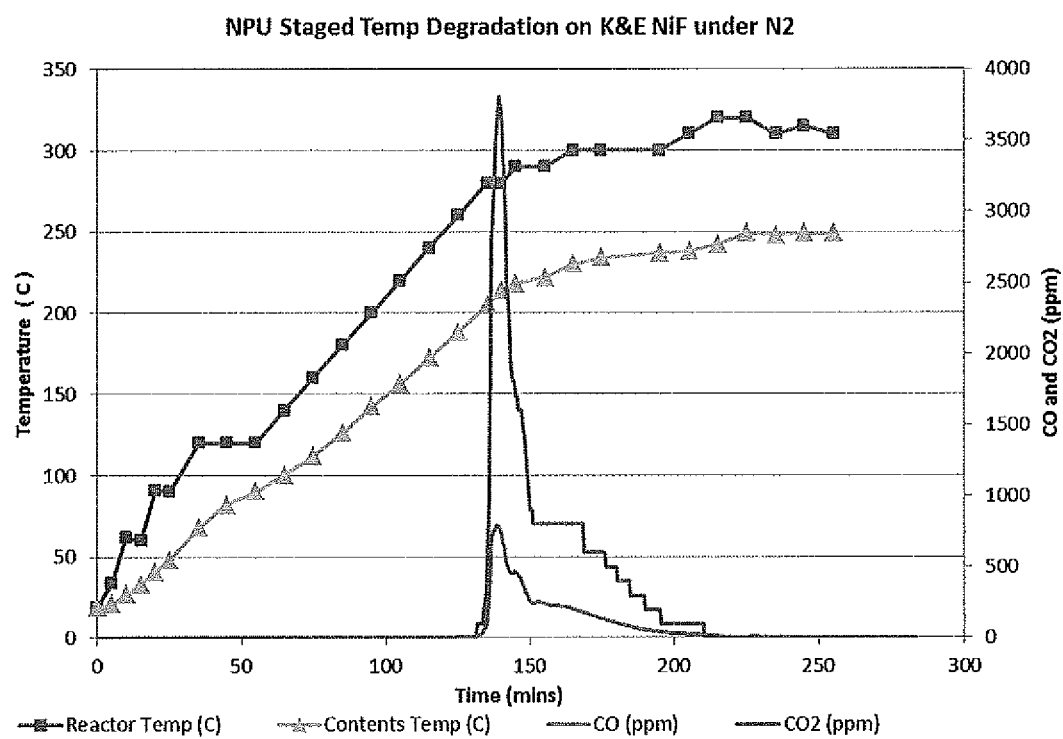
FIG. 1 illustrates temperature and both CO and $CO_2$ concentration versus time during nickel formate degradation, in accordance with various embodiments.

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

This document uses the term "nickel-containing complexation precursor" to refer to material containing a specified portion of its weight as nickel sulfide. The term "nickel metal" followed by a specification on nickel sulfide content is also used to describe this material.

Selected substituents within the compounds described herein are present to a recursive degree. In this context, "recursive substituent" means that a substituent may recite another instance of itself or of another substituent that itself recites the first substituent. Recursive substituents are an intended aspect of the disclosed subject matter. Because of the recursive nature of such substituents, theoretically, a large number may be present in any given claim. One of ordinary skill in the art of organic chemistry understands that the total number of such substituents is reasonably limited by the desired properties of the compound intended. Such properties include, by way of example and not limitation, physical properties such as molecular weight, solubility, and practical properties such as case of synthesis. Recursive substituents can call back on themselves any suitable number of times, such as about 1 time, about 2 times, 3, 4, 5, 6, 7, 8, 9, 10, 15, 20, 30, 50, 100, 200, 300, 400, 500, 750, 1000, 1500, 2000, 3000, 4000, 5000, 10,000, 15,000, 20,000, 30,000, 50,000, 100,000, 200,000, 500,000, 750,000, or about 1,000,000 times or more.

Method of Generating Nickel Metal.

In various embodiments, the present invention provides a method of generating nickel metal. The method can include contacting a nickel starting material with a reductant, e.g., reducing the nickel starting material. The reducing can be performed under conditions sufficient to generate nickel metal having at least about 1500 ppmw sulfur in the form of sulfide.

The reduction (e.g., the contacting of the nickel starting material with the reductant) can include maintaining a temperature for a suitable time, wherein the temperature is high enough to convert the nickel starting material to a nickel that includes sulfur in the form of sulfide. In some embodiments, the reduction can include avoiding surpassing a temperature for particular durations wherein the temperature is high enough to cause significant formation of non-amorphous sulfides, such as non-amorphous nickel sulfides, such as $Ni_3S_2$. As used here, the term "amorphous" refers to material that does not trigger detection by x-ray diffraction (XRD), wherein the x-ray diffraction detection limit referred to has two components which both must be present for detection to occur: (a) about 0.2 wt % concentration of a crystal phase in the bulk of a sample for the crystal phase to be detected and (b) crystallite size of about 5 nm or greater. For example, non-crystalline materials meet this definition, as do nano-crystalline materials and other materials that do not diffract x-ray.

For example, the reduction (e.g., the contacting of the nickel starting material with the reductant) can include maintaining a temperature of about 200° C. to about 350° C., about 225° C. to about 325° C., about 250° C. to about 300° C., about 240° C. to about 310° C., about 250° C. to about 290° C., about 250° C. to about 280° C., about 250° C. to about 270° C., about 250° C. to about 260° C., or about 200° C. or less, or about 205° C., 210, 215, 220, 225, 230, 235, 240, 245, 250, 255, 260, 265, 270, 275, 280, 285, 290, 295, 300, 305, 310, 315, 320, 325, 330, 335, 340, 345, or about 350° C. or more for any suitable time period such as about 1 minute to about 5 days, or about 5 minutes to about 1 day, or about 10 minutes to about 10 hours, or about 20 minutes or less, or about 30 minutes, 40, 50 minutes, 1 hour, 1.5, 2, 2.5, 3, 3.5, 4, 4.5, 6, 6.5, 7, 7.5, 8, 8.5, 9, 9.5, 10, 11, 12, 13, 14, 15, 16, 17, 18, 19, 20, 21, 22, 23, 24 hours, 1.5 days, 2, 3, 4, or about 5 days or more. In various embodiments, the reducing includes not exceeding a temperature of about 250° C. or less, or about 255° C., 260, 270, 275, 280, 285, 290, 295, 300, 305, 310, 315, 320, 325, 330, 335, 340, 345, or about 350° C. or more for any suitable time period such as for more than about 0.1 second, 1 second, 5 seconds, 10, 15, 20, 25, 30, 35, 40, 45, 50, 55 seconds, 1 minute, 2 minutes, 3, 4, 5, 10, 15, 20, 25, 30, 35, 40, 45, 50, 55 minutes, or for 1 hour or more.

The reductant contacted with the nickel starting material during the reducing can be any suitable one or combination of reductants. For example, the reductant can include includes at least one of hydrogen, ammonia, carbon, a $(C_1\text{-}C_{20})$carboxylic acid (or a $(C_1\text{-}C_{20})$alkyl ester or a salt thereof), a formate ester or salt, and carbon-containing compounds (e.g., substituted or unsubstituted $(C_1\text{-}C_{100})$ hydrocarbons). The reductant can include hydrogen, such as hydrogen having any suitable concentration, such as a concentration of 100 vol %, 90, 80, 70, 60, 55, 50, 45, 40, 35, 30, 25, 20, 15, 10, 5, 4, 3, 2, or 1% or less in any suitable medium (e.g., carrier gas), such as in air, nitrogen, carbon dioxide, or in a noble gas such as argon. The carrier gas can be substantially oxygen-free (e.g., free of molecular oxygen, $O_2$). The reductant can be used in stoichiometric excess, such as about 1.5 moles hydrogen to 1.0 mole of nickel, or about 2, 2.5, 3, 3.5, 4, 6, 8, 10, 15, 20, 30, 40, 50, or about 4 moles of hydrogen or more to 1 mole of nickel.

Any suitable type of reactor can be utilized during the reduction of the nickel starting material and during an optional calcination of the nickel starting material or of a nickel-containing precursor to generate the nickel starting material prior to the reduction. For example, a rotary reactor or a fluidized bed reactor can be used.

In various embodiments, the reducing includes contacting the nickel starting material with steam. For example, a gas used for reduction can include steam, which can facilitate generation of a free-flowing nickel metal product. In some embodiments, steam can prevent agglomeration and clumping of the reduced nickel product thereby facilitating product removal from the reaction vessel and further processing of the nickel metal. The proportion of steam in the reducing gas can be any suitable amount, such as about 0.1% to 80% by volume, or about 0.1% to 70% by volume, or about 0.1% to 50% by volume, or from about 0.1% to 30% by volume. The reducing gas can contain about 0.1% to 20% volume percent steam, or about 5% to about 20% steam.

In various embodiments, the reducing (and optionally, calcining) includes handling the reactants such as to minimize or decrease collision impact velocity and compressive forces between particles, such as by rotating or turning the nickel starting material. Fluidized bed reactors can lead to agglomeration of nickel particles, for example, because the particles undergo repeated high impact collisions while being heated to a point where some softening of the particles can occur. Such a process can lead to sintering (agglomeration) of at least some of the particles. Processors other than fluidized bed reactors can lead to the same problems with agglomeration. For example, systems where the nickel particles are significantly compressed against one another such as a screw auger system, which can apply significant compressive force as the particles are moved through the system, can lead to agglomeration of the particles. When the collision impact velocity and compressive forces are minimized between particles a free flowing reduced nickel product can be produced. There are several types of processors that can be employed to avoid nickel particle agglomeration. Examples include rotary type reactors, multiple hearth furnace reactors, and tubular packed reactors operated at close to atmospheric pressure (minimizing compressive forces). Systems that employ spray-dryer type equipment where the particles are highly dispersed in the gas phase to minimize particle-to-particle interaction can also be employed.

In some embodiments, use of a rotary reactor for reduction can have advantages over other types of reactors. For example, high amounts of hydrogen, such as 100 vol % hydrogen, can be employed in a rotary reactor, which can be difficult or impossible in reactors where steam is added to avoid agglomeration (e.g., in fluidized bed reactors). The processing steps can be simple and easier to control in the rotary processor as compared to other reactors. The consumables required for carrying out the processing in a rotary processor can be significantly lower than, for example, a fluidized bed reactor. In some embodiments, the majority of the consumables used in a fluidized bed reactor process are utilized in keeping the bed fluidized. The processing of different raw materials in a fluidized bed system can require evaluating their individual fluidization characteristics, which is costly, time consuming, and not necessarily readily scalable. In comparison, in a rotary unit, there are no such issues in processing different raw materials. Reduction in a rotary reactor can be fast, energy efficient, and can in some embodiments generate an improved product.

In some embodiments, a nickel starting material or nickel-containing precursor can be gently rolled inside a rotary kiln reactor with a co-current or counter-current flow of reducing gases. The reduction can occur at the exposed surface of the particle bed. The exposed surface of the particle bed can be continually refreshed as the kiln rotates. The reducing gases diffuse through the layers of solid particles, so the rate of reaction can be limited by the rate of hydrogen diffusion. The rotary reactor can minimize or decrease compressive or impact forces, and fewer hot spots can be present during the exothermic reduction process. Although steam can in some embodiments be used to avoid or decrease particle agglomeration, the use of a rotary reactor can reduce or minimize the incidence of agglomeration as well as or better than steam, in some embodiments avoiding or decreasing the use of steam.

Nickel Starting Material.

The nickel starting material can be any one or any combination of suitable nickel starting materials, such that performing the method using the nickel starting material produces the nickel having the sulfur in the form of sulfide. The nickel starting material can be any inorganic nickel salt. For example, the nickel starting material, or nickel-containing precursor, can include at least one of basic nickel carbonate, nickel oxide, nickel carbonate, nickel bicarbonate, nickel oxalate, nickel formate, nickel squarate, nickel hydroxide, nickel nitrate, nickel cyanate, nickel sulfate, amorphous $NiS_x$, and crystalline $Ni_3S_2$. In various embodiments the nickel starting material includes nickel formate. The nickel starting material or nickel-containing precursor can include sulfur. The sulfur can be in the form of a reducible sulfur source. The sulfur can be any one or any combination of suitable sulfur materials.

For example, the nickel starting material or nickel-containing precursor can include basic nickel carbonate (e.g., $[Ni(CO_3)_x(OH)_y]_z(H_2O)_n$, wherein x=z (y/2); y=2z−2x; z=1 to 100; and n=0 to 400), nickel carbonate, nickel bicarbonate, nickel oxalate, nickel formate, nickel squarate, nickel hydroxide, nickel oxide, nickel salts, or a combination thereof. In various embodiments, the nickel starting material or nickel-containing precursor can include compounds including $SO_4$ (e.g., $NiSO_4$), or can include elemental sulfur (e.g., $S_8$), $H_2S$, $Ni_3S_2$, $NiS_x$, or amorphous $NiS_x$.

In various embodiments, the method includes contacting the nickel starting material during the reducing with a sulfur source that is different than the nickel starting material, or the nickel starting material can include or can be doped with a sulfur source. For example, the method can include contacting the nickel starting material during the reducing with, or using a nickel starting material that includes or is doped with, elemental sulfur, polymeric sulfur, sulfur-containing gases, sulfur-containing salts, sulfur-containing ions and combinations thereof. The sulfur source can be in liquid, solid, gaseous or a combination of such physical forms. The sulfur source can include, for example, sulfates, sulfites, sulfides, hyposulfites, thiosulfates, sulfur dioxide, sulfur monoxide, sulfur halides, and the like. Examples of sulfur sources that can be employed include hydrogen sulfide, nickel sulfate, nickel sulfite, nickel sulfide, nickel hyposulfite, nickel thiosulfate, sulfur trioxide, sulfur dioxide, sulfur monoxide, disulfur dichloride, sulfur dichloride, sulfur tetrachloride, sulfur chloride pentafluoride, disulfur decafluoride, sulfur hexafluoride, sulfur tetrafluoride, sulfur trifluoride and combinations thereof. Any of these and other sources of sulfur can be used to activate nickel for complex formation with phosphorus-containing ligands. Any suitable amount of one or more sulfur sources can be contacted with the nickel starting material during the reducing, and the nickel starting material can be doped with any suitable amount of one or more sulfur sources, such as about 0.000,01 wt % to about 100,000 wt % relative to the total amount of nickel starting material and one or more sulfur sources present, or about 0.01 wt % to about 1000 wt %, or about 0.000,01 wt % or less, or about 0.000,1 wt %, 0.001, 0.01, 0.1, 1, 2, 3, 4, 5, 10, 15, 20, 25, 30, 35, 40, 45, 50, 60, 70, 80, 90, 100, 150, 200, 250, 500, 750, 1,000, 2,000, 5,000, 10,000, 25,000, 50,000, 75,000, or about 100,000 wt % or more.

Elemental sulfur can be present in a number of forms, including solid elemental sulfur, gaseous sulfur, polymeric sulfur, mixtures of polymeric chains of sulfur, cyclic sulfur and combinations thereof. There are also a large number of allotropes of sulfur. The most common form found in nature is yellow orthorhombic α-sulfur, which contains puckered rings of eight sulfur atoms ($S_8$). In addition, other solid forms of sulfur contain sulfur rings of 6, 7, 9-15, 18 and 20 atoms. There are also sulfur gases, such as $S_2$, $S_3$, $S_4$, and $S_5$. Metallic-like sulfur forms can also be formed, for example, at high-pressures. Any and all of these forms of sulfur are sulfur sources for use in the methods described herein.

The sulfur source may be a sulfur-donor. Examples of sulfur donating compounds include thioethers, thioesters, disulfides and the like. For example, the disulfide can be selected from disulfides, thioacetic acid, thioacetate salts, polysulfides, bis-alkylamino disulfides, sulfenic sulfonic thioanhydrides, thiosulfonate salts, aminothiosulfonates, acylmethylmercapto azoles or azolium salts, thiazepines, thiepins, 1,4-dithiins, 1,2-, 1,3-, or 1,4-thiazines, 1,4,2-dithiazines, 1,3,4-, 1,2,6-, 1,3,5-thiadiazines, dihydro-derivatives of dithiazines or thiadiazines, 1,2,3,4-thiatriazoles and combinations thereof.

In some embodiments, the method can include calcining the nickel starting material, or calcining a nickel-containing precursor to form the nickel starting material, prior to the reducing. As used herein "calcine" or "calcining" or "calcination" is a thermal treatment process applied to nickel starting materials or nickel-containing precursors in order to bring about a thermal decomposition, phase transition, or removal of a volatile fraction. Calcination can be performed using any available calcination procedure or apparatus in presence of appropriate gas environment such as air or nitrogen, or in other suitable media, or even in absence of gas environment such as partial or total vacuum.

For example, calcination can be used to prepare a nickel starting material for reduction, and can be used to form a nickel starting material from a nickel-containing precursor. Reduction can be performed after calcination. A calcination can be carried out using conditions sufficient to calcine the nickel starting material or nickel-containing precursor. The calcination can be performed under conditions sufficient to substantially remove volatile materials. Such volatile materials include carbon dioxide, nitrate, nitric acid, formate, formic acid, cyanate, hydrogen cyanide, sulfate, sulfuric acid, water and the like. For example, carbon dioxide or carbon dioxide and water can be the major volatile materials that are removed, particularly when the nickel starting material or nickel-containing precursor is or includes basic nickel carbonate. The calcination can be performed under conditions sufficient to convert a nickel starting material or nickel-containing precursor into nickel(II) oxide (NiO).

Calcination can be carried out in any suitable reactor, such as a fluid bed reactor, a fixed bed reactor, an expanded fixed bed, or a rotary processor such as a rotary reactor, a rotary kiln, or a rotary pan. Calcination can conveniently be performed in a rotary processor. In some embodiments, a nickel starting material can be reduced in the same rotary processor as was used for calcination pursuant to the methods described herein.

Calcination can be carried out in any gas or atmosphere that does not react with nickel-containing salts or compounds to form undesirable nickel-containing materials. The gas or atmosphere can contain oxygen. Suitable convenient gases for the calcination step include an atmosphere that contains oxygen (e.g., air), nitrogen, argon, or helium. Temperatures useful for calcination can include those in the range of about 200° C. to 600° C. Below about 200° C. or about 250° C., the calcination can be incomplete, so that the nickel-containing precursor is not completely converted to the nickel starting material, or such that the nickel starting material is not completely calcined prior to the reduction. A partially-calcined material can contain volatile materials that can reduce the activity of the nickel metal product. Above 600° C., excessive collapse or sintering of the nickel-containing precursor or nickel starting material may occur under some conditions, consequentially reducing the reactivity of the nickel powder product.

The time for optimal calcination can vary inversely with the temperature: when lower temperatures are used (e.g., 250° C.) calcination can be performed for longer time periods (e.g., up to 18-20 hours). However, when calcination is performed at temperatures of about 300° C. to 600° C., a shorter time period is effective for calcination, for example, about 10 minutes to about 6 hours, or about 10 minutes to 4 hours. The time for the calcination step can range from tens of seconds at 600° C. to multiple hours at 250° C. In general, calcination can be complete within about 30 minutes to 2 hours when using temperatures of about 350° C. to 500° C. Especially desirable calcinations temperatures are from about 400° C. to about 500° C. At temperatures between 450° C. and 500° C., calcination can be substantially complete within about 1-2 hours.

Effective calcination can be monitored and detected by observing the release of volatile components such as carbon dioxide and/or by observing the conversion of nickel(II)-containing salts and compounds within the composition to nickel oxide (and/or nickel hydroxide). Calcination can therefore continue until volatile materials (e.g. carbon dioxide and/or water) are no longer detected in the effluent gases emerging from the calcination chamber. In some cases, calcination can be continued for 5-60 minutes after volatile materials is no longer detected in the effluent gases emerging from the calcination chamber. For example, calcination can continue for 5-30 minutes, or for 5-20 minutes, or for 5-15 minutes after volatile materials are no longer detected in the effluent gases emerging from the calcination chamber.

After calcination is completed, the flow of oxygen-containing gas can be terminated and the apparatus can be flushed with a non-oxygen-containing or inert gas. Nitrogen is useful for this purpose but other non-oxygen-containing or inert gases can also be used (e.g., noble gases such as argon or neon). The flow of the non-oxygen containing or inert gas is continued until oxygen is substantially removed from the reactor bed of the apparatus. The reduction of nickel in the calcination product can then be performed.

In some embodiments, the method can include precipitating the nickel starting material prior to the reducing.

In various embodiments, the nickel starting material or nickel-containing precursor or can be made by (i) contacting a precipitant solution and a nickel solution in a precipitation reactor to form a reaction mixture; and (ii) precipitating the nickel salt from the reaction mixture, wherein the nickel solution comprises nickel(II) ions and water, and the precipitant solution is selected from the group consisting of: (a) bicarbonate ions and water, (b) carbonate ions and water, and (c) mixtures thereof.

The mole ratio of bicarbonate ions to nickel(II) ions in the reaction mixture at the conclusion of the feeding can range from 0:1 to 2:1, including from about 0:1 to about 1.6:1, from about 0:1 to about 1.2:1, from about 1.0:0 to about 1.9:1, from about 1.2:1 to about 1.9:1, from about 0.8:1 to about 1.4:1, from about 1.0:1 to about 1.8:1, from about 1.0:1 to about 1.6:1, from about 1.0:1 to about 1.4:1, from about 0.8:1 to about 1.4:1, and from about 0.8:1 to about 1.2:1. The mole ratio of carbonate ions to nickel ions in the reaction mixture at the conclusion of the feeding can range from 0:1 to 1.6:1, including from about 0:1 to about 1.4:1, from about 1.0:0 to about 1.2:1, from about 0.8:1 to about 1.4:1, from about 1.0:1 to about 1.6:1, from about 1.0:1 to about 1.6:1, from about 1.0:1 to about 1.4:1, from about 0.8:1 to about 1.4:1, and from about 0.8:1 to about 1.2:1. Blends of bicarbonates and carbonates can also be used in the precipitant solution.

The precipitation reactor used for preparing nickel starting material or nickel-containing precursor can be any suitable containment vessel such as a tank, vessel or pipe. The precipitation can be performed in a batch or continuous fashion. Further, the reaction mixture can be agitated prior to and/or during the precipitation. For example, agitation can be done by mechanical stirring, pumped circulation loop, flow-through static mixture, or ultrasound. The use of high sheer during precipitation can prevent particle agglomeration and can give smaller resulting particles. Reactor designs, stirring designs, and the application of high amounts of power to stirring are examples of factors that can cause a high-sheer stirring of the reaction mixture during precipitation.

The precipitation can be performed within a temperature range of from about 0° C. to about 90° C., including from about 20° C. to about 90° C., from about 20° C. to about 70° C., from about 20° C. to about 50° C., from about 50° C. to about 90° C., from about 60° C. to about 80° C., and from about 65° C. to about 75° C. In some embodiments, increased temperature during precipitation can decrease the proportion of carbonate ions in the resulting nickel starting material or nickel-containing precursor.

The nickel composition can be precipitated from the reaction mixture in the presence of added carbon dioxide. For example, the carbon dioxide can be added to the precipitation reactor, added to the nickel solution, added to the precipitant solution, added to the reaction mixture, and any combination thereof. The precipitant solution can be fed to the precipitation reactor over a period of from about 30 minutes to about 60 minutes, and such addition can be performed in a semi-continuous or continuous manner. Further, the precipitant solution can be added to the nickel solution in the precipitation reactor in a semi-continuous or continuous manner, for example, using gradual addition. In some embodiments, the use of a higher pH during precipitation can decrease the proportion of carbonate ions in the resulting precipitate. For example, a pH value of about 4, 5, 6, 7, 8, or about 9, or higher may be used. In one example, the pH increases from about 4.9 to about 5.8 during the precipitation.

The reaction mixture can also be digested after contacting the precipitant solution to the nickel solution by heating the reaction mixture from between about 50° C. and about 90° C. for a period of from about 0.25 hours to about 24 hours. In some embodiments, precipitation can occur before, during, or after digestion, or any combination thereof. Other suitable temperature ranges include from about 60° C. to about 80° C., and/or from about 65° C. to about 75° C. Other suitable digestion time periods can range from about 2 hours to about 24 hours, including from about 4 hours to about 20 hours, from about 6 hours to about 16 hours, and from about 8 hours to about 12 hours. In some embodiments, longer digestion times can cause larger particles in the resulting precipitate.

After the precipitation, optionally, the precipitated nickel composition can be washed with water, and the precipitated nickel composition can be at least partially dried. For example, the precipitant can be separated from the reaction mixture by filtration or decantation, washed with water by filtration or decantation, and dried by water evaporation between 60° C. and 100° C. Drying can be performed under any suitable conditions, such as ambient pressure or under vacuum, and in the presence of an inert gas such as nitrogen.

A nickel solution used in preparation of the precipitant, comprising nickel(II) ions and water, can be prepared by dissolving a nickel(II) salt in water. The nickel salt can be any salt that is soluble in water, for example $NiCl_2$, $NiSO_4$, and $Ni(NO_3)_2$. Alternatively, a commercial nickel starting material or nickel precursor (e.g., BNC nickel) can be repurified, by first dissolving in an aqueous acid such as hydrochloric, sulfuric, or nitric acid, then using that solution for re-precipitation as described herein. Other water-insoluble Ni(II) sources can be converted to a soluble material in a similar manner and subsequently subjected to precipitation.

The precipitant solution, comprising bicarbonate ions, can be prepared by dissolving a bicarbonate salt, for example, $NaHCO_3$ and $NH_4HCO_3$, in water. Alternatively, the precipitant solution can be prepared in-situ by dissolving $CO_2$ and an alkali metal hydroxide or ammonia in water by known methods. Likewise, the precipitant solution, comprising carbonate ions, can be prepared by dissolving a carbonate salt, for example $Na_2CO_3$. The precipitant solution can also be prepared in-situ by dissolving $CO_2$ and an alkali metal hydroxide in water by known methods. The anion of the nickel salt and cation of the bicarbonate or carbonate salt may be selected such that a salt produced from the precipitation, comprising both the cation and anion from the reaction mixture (for example NaCl), is soluble in the water of the reaction mixture. Such a selection provides a method for separating the anions and cations from the precipitant.

The amount of bicarbonate or carbonate ions relative to the nickel(II) ions charged to make the precipitant can affect the nickel reactivity of the resulting zero-valent nickel with the phosphorus-containing ligand (e.g., ligand (V)). In various embodiments, surprisingly, the use of excess precipitant solution produces nickel metal of low reactivity for the phosphorous-ligand complex reaction. Highly reactive nickel can produced when reduced levels of precipitant are used, where presumably more of the nickel(II) ions are allowed to remain dissolved in the water of the resulting reaction mixture and may not be precipitated.

In various embodiments, a precipitant made using bicarbonate ions can filter and surprisingly washes faster than a precipitated nickel composition made using carbonate ions. A filtered precipitated nickel composition made using bicarbonate ions can dry to a soft powder with little shrinkage. For these reasons, producing the nickel-containing solid using bicarbonate ions provides further desirable properties for downstream processing and handling of the dried precipitated nickel composition.

Nickel Including Sulfur in the Form of Sulfide.

Various embodiments of the present invention provide a nickel metal including sulfur in the form of sulfide. The nickel metal can be any suitable nickel metal (e.g., $Ni^0$) having the characteristics described herein. The nickel can be any nickel produced by any embodiment of a method of the present invention. The nickel metal can include any suitable one or combination of materials other than $Ni^0$, in any suitable proportion, such that the $Ni^0$ therein can form nickel-ligand complexes as described herein. The nickel metal can be about 50 wt % to about 99.999,99 wt % $Ni^0$, about 85 wt % to about 99.999,99 wt % $Ni^0$, or about 50 wt % or less, or about 55 wt %, 60, 65, 70, 75, 80, 81, 82, 83, 84, 85, 86, 87, 88, 89, 90, 91, 92, 93, 94, 95, 96, 97, 98, 99, 99.9, 99.99, 99.999, 99.999,9, or about 99.999,99 wt % or more $Ni^0$.

As used herein, sulfur in the form of sulfide refers to a sulfur atom having a charge of −2, e.g., $S^{-2}$. The nickel metal including sulfur in the form of sulfide can have any suitable proportion of sulfur in the form of sulfide, such as from about 500 ppmw to about 70,000 ppmw, for example, from about 1000 ppmw to about 60,000 ppmw, from about 1,500 ppmw to about 50,000 ppmw, from about 3,000 ppmw to about 30,000 ppmw, from about 5,000 ppmw to about 10,000 ppmw. The sulfur in the nickel can include sulfur in any form, so long as at least some of the sulfur is in the form of sulfide. In addition to the sulfur in the form of sulfide, the nickel metal can include any other suitable negatively charged ions, in any suitable concentration such that the nickel metal can be used as described herein, such as a halide (e.g., as fluoride, chloride, iodide, or bromide), nitrate, hydrogen sulfate, dihydrogen phosphate, bicarbonate, nitrite, perchlorate, iodate, chlorate, bromate, chlorite, hypochlorite, hypobromite, cyanide, amide, cyanate, hydroxide, permanganate, a conjugate base of any suitable carboxylic acid (e.g., acetate or formate), oxide, sulfide, nitride, arsenate, phosphate, arsenite, hydrogen phosphate, sulfate, thiosulfate, sulfite, carbonate, chromate, dichromate, peroxide, oxalate, or any combination thereof. In some embodiments, the nickel metal includes substantially no other negatively charged ions.

The counterion for the $S^{-2}$ can be any other suitable counterion or combination of counterions. For example, the counterion or combination of counterions can include hydrogen ($H^+$), ammonium($NH_4^+$), an alkali metal such as sodium (Na+), potassium ($K^+$), lithium ($Li^+$), a counterion with a positive charge greater than +1 such as $Zn^{2+}$, $Al^{3+}$, or alkaline earth metals such as $Ca^{2+}$, $Mg^{2+}$, suitable ions of any of Al, As Ca, Cd, Co, Cr, Cu, Fe, Mg, Pb, Si, Na, K, and Zn, or any combination thereof. In some embodiments, the counterion for the sulfur in the form of sulfide is nickel or includes nickel, such as $Ni^{+2}$. In some embodiments, the counterion is nickel having a charge other than +2 (e.g., $Ni^{+1}$, $Ni^{+3}$, $Ni^{+4}$, or another charge) and is combined with other materials (e.g., any suitable counterion, such as any counterion listed herein) such as other nickel ions, such that the combination of counterions has a +2 charge. The sulfur in the form of sulfide can be nickel sulfide. As used herein, nickel sulfide refers to a sulfide (e.g., $S^{-2}$) that has one or more nickel atoms as counterions. In some examples, the nickel sulfide can be stoichiometric nickel sulfide (e.g., NiS). In some examples, the nickel sulfide can be nonstoichiometric, and can have a unit formula of $NiS_X$, wherein the nickel has any suitable oxidation state such that overall the compound has a neutral charge, wherein X is about 0.1 to about 5, about 0.5 to about 1.5, or about 0.1 or less, or about 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.2, 2.4, 2.6, 2.8, 3, 3.2, 3.4, 3.6, 3.8, 4, 4.5, or about 5 or more. In various embodiments, nickel sulfide is referred to as $NiS_X$.

The nickel sulfide can be amorphous nickel sulfide. As used herein, amorphous nickel sulfide refers to nickel sulfide that lacks XRD-detectable long-range order characteristic of a crystal. An amorphous nickel sulfide can have short-range order, such as on an atomic length scale. An amorphous nickel sulfide can lack a consistent repeating unit cell or lattice pattern. When exposed to X-rays, the amorphous nickel sulfide can have a poorly defined pattern, since the components are not arranged in a regular array. The amorphous nickel sulfide can lack a specific melting point, due to the lack of a consistent and repeated chemical environment around each atom. The distinction between crystalline or amorphous structure can be made by establishing whether or not the scattering pattern by XRD shows broad intensity corresponding to a known crystal structure. For nickel sulfide the practical detection limit for crystallite size determination of the $Ni_3S_2$ phase using XRD is 5 nm providing the sulfide phase content of the Nickel is at least 0.2 wt % or above the phase detection limit of the XRD instrument employed whichever is the lower. Thus, nickel sulfide with a crystallite size of below 5 nm falls within the definition of amorphous nickel sulfide. Nickel sulfide with less than 0.2 wt % crystalline phase falls within the definition of amorphous nickel sulfide.

The nickel metal can have any suitable properties such as surface area, crystallite size, crystallite size distribution, and surface crystallite distribution, such that the nickel metal can be used as described herein (e.g., such that the nickel metal can form nickel-ligand complexes). In various embodiments, the nickel metal meets at least one of the following measurements: the nickel metal has a BET Specific Surface Area/C50 ratio of not less than $0.07 \times 10^9$ m/gm; at least 10% of the nickel crystallites have a size (C10) that is less than about 20 nm; the nickel crystallites have an average crystallite size of no greater than about 30 nm; the nickel crystallite size distribution span is greater than about 1.0; the nickel metal on average has at least about $10^{15}$ surface crystallites per gram of nickel; the nickel metal has a BET Specific Surface Area of at least about 1 $m^2$/gm; at least 10% of the particles of the form have a size (D10) of no greater than about 6 μm; the nickel metal has a Laser Diffraction Specific Surface Area of at least about 0.4 $m^2$/gm; the nickel metal has a BET Specific Surface Area to D10 ratio of about $0.3 \times 10^6$ m/gm to about $10.0 \times 10^6$ m/gm; on average there are at least about $10^{31}$ surface crystallites per gram nickel that are smaller than or equal to size C10; an equilibrium concentration of 1000-6000 ppm of soluble Ni as Ni-Ligand (V) complex is typically reached when 1-5 wt % of the nickel metal is mixed with 3-pentenenitrile containing approximately 5-10 wt % Ligand (V) and 0.3-1.5% $ZnCl_2$ at a reaction temperature of 40-80° C.; wherein Ligand (V) has the following formula:

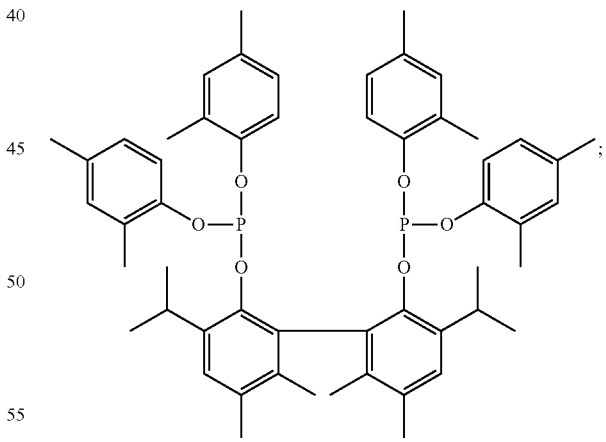

and any combination thereof.

In various embodiments, the nickel metal meets a combination of at least one particle size measurement and at least one crystallite size measurement, or at least one particle size measurement and at least one surface area measurement, or at least one crystallite size measurement and at least one surface area measurement, at least one particle size measurement and at least one crystallite size measurement and at least one surface area measurement. Particle size measurements can include: maximum particle size, such as maximum particle size of a particular proportion of the particles (e.g., at least 10% of the particles of the form can have a size (D10) of no greater than about 6 μm). Crystallite size measurements can include: maximum nickel crystallite sizes (e.g., the nickel crystallites can have an average crystallite size of no greater than about 30 nm); minimum surface crystallites per mass (e.g., the nickel metal on average can have at least about $10^{15}$ surface crystallites per gram of nickel); minimum surface crystallites of a particular size per mass (e.g., on average there can be at least about $10^{31}$ surface crystallites per gram nickel that are smaller than or equal to size C10); maximum crystallite size, such as maximum crystallite size of a particular proportionof the crystallites (e.g., at least 10% of the nickel crystallites can have a size (C10) that is less than about 20 nm); and minimum crystallite size distribution span (e.g., the nickel crystallite size distribution span can be greater than about 1.0). Surface area measurements can include: minimum surface area (e.g., the nickel metal can have a BET Specific Surface Area of at least about 1 $m^2$/gm, or the nickel metal can have a Laser Diffraction Specific Surface Area of at least about 0.4 $m^2$/gm); and maximum surface area to particle size ratio (e.g., the nickel metal can have a BET Specific Surface Area/C50 ratio of not less than $0.07 \times 10^9$ m/gm, or the nickel metal can have a BET Specific Surface Area to D10 ratio of about $0.3 \times 10^6$ m/gm to about $10.0 \times 10^6$ m/gm).

In various embodiments, the nickel metal has a BET Specific Surface Area of at least about 10 $m^2$/gm, or a Laser Diffraction Specific Surface Area of at least about 0.4 $m^2$/gm, or both. Also, at least 10% of the nickel particles (D10) can in some embodiments have a diameter of no greater than about 4 μm.

In various embodiments, the nickel metal includes crystallites (e.g., regions of local crystalline order within larger more disordered particles) wherein an average crystallite size (diameter) is no greater than about 20-25 nm.

In various embodiments, the surface characteristics of nickel metal particles composed of the crystallites are such that a ratio of BET Specific Surface Area to Laser Desorption Specific Surface Area is between 15 and 25, and/or a ratio of BET Specific Surface Area to D10 is about $0.3 \times 10^6$ m/gm to about $10.0 \times 10^6$ m/gm, or about $0.5 \times 10^6$ m/gm to about $5 \times 10^6$ m/gm.

In some embodiments, the nickel metal can have a BET Specific Surface Area of at least about 1 $m^2$/gm. In various embodiments, the nickel metal can have a BET Specific Surface Area greater than 5 $m^2$/gm. In further embodiments, the nickel particular form has a BET Specific Surface Area of greater than about 10 $m^2$/gm, or greater than 11 $m^2$/gm, or greater than 12 $m^2$/gm, or greater than 13 $m^2$/gm, or greater than 14 $m^2$/gm, or greater than 15 $m^2$/gm, or greater than 16 $m^2$/gm, or greater than 17 $m^2$/gm, or greater than 18 $m^2$/gm, or greater than 19 $m^2$/gm. In some embodiments, the nickel metal can have a BET Specific Surface Area greater than 20 $m^2$/gm. For example, the nickel particular form can have a BET Specific Surface Area of about 1 $m^2$/gm to about 40 $m^2$/gm, or any numerical value between 1-40 $m^2$/gm, or between 10-50 $m^2$/gm.

In some embodiments, the nickel metal has a BET Specific Surface Area of at least about 0.1 $m^2$/gm, or at least about 0.2 $m^2$/gm, or at least about 0.3 $m^2$/gm, or at least about 0.4 $m^2$/gm, or at least about 0.5 $m^2$/gm, or at least about 0.6 $m^2$/gm, or at least about 0.7 $m^2$/gm, or at least about 0.8 $m^2$/gm, or at least about 0.9 $m^2$/gm, or at least about 1 $m^2$/gm. It will be understood that the skilled person may run trial-and-error experiments to optimize the nickel metal BET Specific Surface Area.

In various embodiments, the nickel crystallite size distribution span is greater than 1.5, and/or the C10 value is less than about 10 nm after reduction at 300-400° C., or both. Crystallite size is typically measured as a diameter of the crystallite, for example, along the major dimension. In some embodiments, the nickel metal can include nickel crystallite sizes with diameters in the range of 0.1 to 10 nm.

In various embodiments, on average per gram there are at least about $5 \times 10^{15}$ surface crystallites present on a nickel particle. In various embodiments, on average there are at least about $5 \times 10^{15}$ surface crystallites present per gram nickel.

In various embodiments, the nickel metal can be substantially dry, for example, a powder or particulate form. In other embodiments, the nickel metal can be suspended or substantially dissolved in a solvent. The solvent can be a non-aqueous solvent. The solvent can be an organic solvent.

Nickel-Ligand Complex.

In various embodiments, the method can include forming a complex between nickel atoms of the nickel metal product having sulfur in the form of sulfide and one or more ligands, such as one or more phosphorus-containing ligands. The nickel-ligand complex can function as a catalyst for various reactions, such as hydrocyanation of conjugated dienes to mononitriles, and for the hydrocyanation of unsaturated nitriles to provide dinitriles (e.g., adiponitrile).

The nickel-ligand complex can include nickel and at least one phosphorus-containing (P-containing) ligand. The P-containing ligand can, for example, be a phosphite, a phosphonite, a phosphinite, a phosphine, and a mixed P-containing ligand or a combination of such members. The P-containing ligands can be monodentate or multidentate, for example, bidentate or tridentate.

The term "monodentate" is known in the art and means only one phosphorus atom of the ligand can be bonded to a single metal atom. In some embodiments, two monodentate ligands can separately be bonded to the metal atom, or one monodentate ligand and one multidentate ligand can each be bonded to the metal atom. The term "bidentate" is known in the art and means both phosphorus atoms of the ligand can be bonded to a single metal atom. A bidentate P-containing ligand can, for example, be selected from the group consisting of a bidentate phosphite, a bidentate phosphonite, a bidentate phosphinite, a bidentate phosphine, and a mixed bidentate ligand. A mixed bidentate ligand can, for example, be selected from the group consisting of a phosphite-phosphonite, a phosphite-phosphinite, a phosphite-phosphine, a phosphonite-phosphinite, a phosphonite-phosphine, and a phosphinite-phosphine. The term "tridentate" means the three phosphorus atoms on the ligand can be bonded to a single metal atom. The terms "bidentate" and "tridentate" are also known in the art as chelate ligands.

The phosphorous-containing ligand can be a monodentate phosphite, monodentate phosphonite, monodentate phosphinite, monodentate phosphine, bidentate phosphite, bidentate phosphonite, bidentate phosphinite, or bidentate phosphine, and any combination of these members. Further, the phosphorous-containing ligand can be a monodentate phosphite to form the nickel complex of the monodentate phosphite, then the nickel complex of the monodentate phosphite can be combined with a bidentate phosphorous-containing ligand. Likewise, the phosphorous-containing ligand can be a bidentate phosphite further comprising a monodentate phosphite.

Suitable phosphorus-containing ligands for the catalyst include those selected from the group consisting of compounds of Formula (III), Formula (IV), Formula (IVa) or combinations thereof. Formula (III) has the structure:

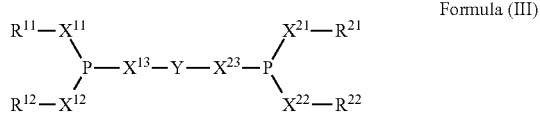

The variables $X^{11}$, $X^{12}$, $X^{13}$, $X^{21}$, $X^{22}$ and $X^{23}$ can independently represent oxygen or a single (direct) bond. The variables $R^{11}$ and $R^{12}$ can independently represent identical or different, single or bridged organic radicals. The variables $R^{21}$ and $R^{22}$ can independently represent identical or different, single or bridged organic radicals. The variable Y can represent a bridging group.

In some embodiments, the variables $X^{11}$, $X^{12}$, $X^{13}$, $X^{21}$, $X^{22}$ and $X^{23}$ can each be oxygen. In such a case, the bridging group Y is bonded to phosphite groups. In another embodiment, $X^{11}$ and $X^{12}$ can each be oxygen and $X^{13}$ a single bond, or $X^{11}$ and $X^{13}$ each oxygen and $X^{12}$ a single bond, so that the phosphorus atom surrounded by $X^{11}$, $X^{12}$ and $X^{13}$ is the central atom of a phosphonite. In such a case, $X^{21}$, $X^{22}$ and $X^{23}$ can each be oxygen, or $X^{21}$ and $X^{22}$ can each be oxygen and $X^{23}$ a single bond, or $X^{21}$ and $X^{23}$ can each be oxygen and $X^{22}$ a single bond, or $X^{23}$ can be oxygen and $X^{21}$ and $X^{22}$ each a single bond, or $X^{21}$ can be oxygen and $X^{22}$ and $X^{23}$ each a single bond, or $X^{21}$, $X^{22}$ and $X^{23}$ can each be a single bond, so that the phosphorus atom surrounded by $X^{21}$, $X^{22}$ and $X^{23}$ can be the central atom of a phosphite, phosphonite, phosphinite or phosphine, preferably a phosphonite. In another embodiment, $X^{13}$ can be oxygen and $X^{11}$ and $X^{12}$ each be a single bond, or $X^{11}$ can be oxygen and $X^{12}$ and $X^{13}$ each a single bond, so that the phosphorus atom surrounded by $X^{11}$, $X^{12}$ and $X^{13}$ is the central atom of a phosphonite. In such a case, $X^{21}$, $X^{22}$ and $X^{23}$ can each be oxygen, or $X^{23}$ can be oxygen and $X^{21}$ and $X^{22}$ each a single bond, or $X^{21}$ can be oxygen and $X^{22}$ and $X^{23}$ each a single bond, or $X^{21}$, $X^{22}$ and $X^{23}$ can each be a single bond, so that the phosphorus atom surrounded by $X^{21}$, $X^{22}$ and $X^{23}$ can be the central atom of a phosphite, phosphinite or phosphine, preferably a phosphinite. In another embodiment, $X^{11}$, $X^{12}$ and $X^{13}$ can each be a single bond, so that the phosphorus atom surrounded by $X^{11}$, $X^{12}$ and $X^{13}$ is the central atom of a phosphine. In such a case, $X^{21}$, $X^{22}$ and $X^{23}$ can each be oxygen, or $X^{21}$, $X^{22}$ and $X^{23}$ can each be a single bond, so that the phosphorus atom surrounded by $X^{21}$, $X^{22}$ and $X^{23}$ can be the central atom of a phosphite or phosphine, preferably a phosphine. The bridging group Y is particularly an arylene group which is substituted, for example by $C_1$-$C_4$-alkyl, halogen, such as fluorine, chlorine, bromine, halogenated alkyl, such as trifluoromethyl, arylene, such as phenylene, or is unsubstituted, such as a group having from 6 to 20 carbon atoms in the aromatic system, in particular pyrocatechol, bis(phenol) or bis(naphthol). The $R^{11}$ and $R^{12}$ radicals can each independently be identical or different organic radicals. The $R^{11}$ and $R^{12}$ radicals can be aryl radicals, such as those having from 6 to 10 carbon atoms, which can be unsubstituted or mono- or polysubstituted, in particular by $C_1$-$C_4$-alkyl, halogen, such as fluorine, chlorine, bromine, halogenated alkyl, such as trifluoromethyl, aryl, such as phenyl, or unsubstituted aryl groups. The $R^{21}$ and $R^{22}$ radicals can each independently be identical or different organic radicals. The $R^{21}$ and $R^{22}$ radicals can be aryl radicals, particularly those having from 6 to 10 carbon atoms, which can be unsubstituted or mono- or polysubstituted, in particular by $C_1$-$C_4$-alkyl, halogen, such as fluorine, chlorine, bromine, halogenated alkyl, such as trifluoromethyl, aryl, such as phenyl, or unsubstituted aryl groups. The $R^{11}$ and $R^{12}$ radicals can each be separate or bridged. The $R^{21}$ and $R^{22}$ radicals can also each be separate or bridged. The $R^{11}$, $R^{12}$, $R^{21}$ and $R^{22}$ radicals can each be separate, two can be bridged and two separate, or all four can be bridged, in the manner described.

Formula (IV) has the structure,

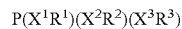

The variables $X^1$, $X^2$ and $X^3$ can independently represent oxygen or a single direct bond. The variables $R^1$, $R^2$ and $R^3$ can each independently be identical or different organic radicals.

The variables $R^1$, $R^2$ and $R^3$ can be each independently alkyl radicals preferably having from 1 to 10 carbon atoms, such as methyl, ethyl, n-propyl, i-propyl, n-butyl, i-butyl, s-butyl, t-butyl, or aryl groups such as phenyl, o-tolyl, m-tolyl, p-tolyl, 1-naphthyl, 2-naphthyl, or hydrocarbyl, preferably having from 1 to 20 carbon atoms, such as 1,1'-biphenol, 1,1'-binaphthol. The $R^1$, $R^2$ and $R^3$ groups can be bonded together directly (e.g., not solely via the central phosphorus atom). In an embodiment, $R^1$, $R^2$ and $R^3$ groups are radicals selected from the group consisting of phenyl, o-tolyl, m-tolyl and p-tolyl. In a particular embodiment, a maximum of two of the $R^1$, $R^2$ and $R^3$ groups are phenyl groups. In another embodiment, a maximum of two of the $R^1$, $R^2$ and $R^3$ groups are o-tolyl groups. Particular compounds which can be used are those of the formula (IVa):

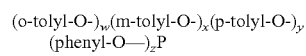

The variables w, x, y, z can each be a natural number, wherein w+x+y+z=3 and z is less than or equal to 2. Examples of such compounds (IVa) are (o-tolyl-O—)$_3$P, (p-tolyl-O-)(phenyl-O—)$_2$P, (m-tolyl-O—) (phenyl-O—)$_2$P, (o-tolyl-O-)(phenyl-O—)$_2$P, (p-tolyl-O-)$_2$(phenyl-O—)P, (m-tolyl-O-)$_2$(phenyl-O—)P, (o-tolyl-O-)$_2$(phenyl-O—)P, (m-tolyl-O-)(p-tolyl-O—) (phenyl-O—)P, (o-tolyl-O-)(p-tolyl-O-)(phenyl-O—)P, (o-tolyl-O-)(m-tolyl-O—) (phenyl-O—)P, (p-tolyl-O—)$_3$P, (m-tolyl-O-)(p-tolyl-O—)$_2$P, (o-tolyl-O-)(p-tolyl-O—)$_2$P, (m-tolyl-O-)$_2$(p-tolyl-O—)P, (o-tolyl-O-)$_2$(p-tolyl-O—)P, (o-tolyl-O-)(m-tolyl-O-)(p-tolyl-O—)P, (m-tolyl-O—)$_3$P, (o-tolyl-O-)(m-tolyl-O—)$_2$P, (o-tolyl-O-)$_2$(m-tolyl-O—)P, or mixtures of such compounds.

An example of a useful bidentate phosphite ligand has Formula (V):

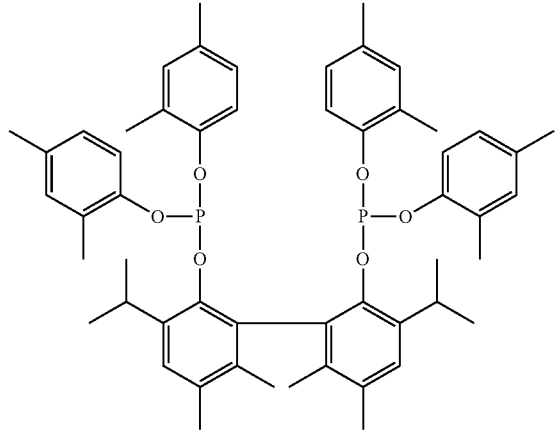

Formula (V)

Further examples of bidentate phosphite ligands include those having the Formulae (VI) to (IX), shown herein wherein for each formula, $R^{17}$ can be selected from the group consisting of methyl, ethyl, and isopropyl, and $R^{18}$ and $R^{19}$ can be independently selected from H or methyl:

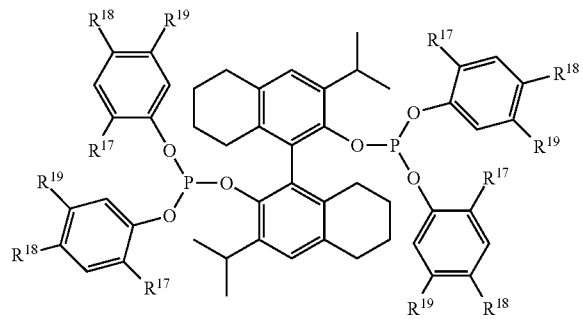

(VI)

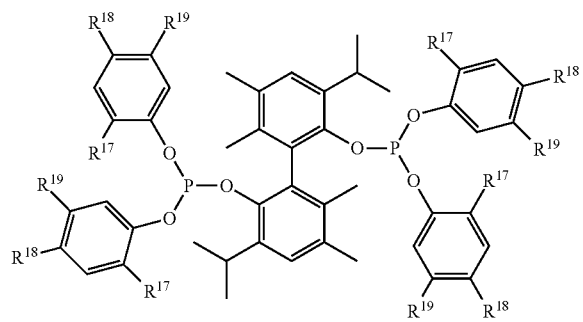

(VII)

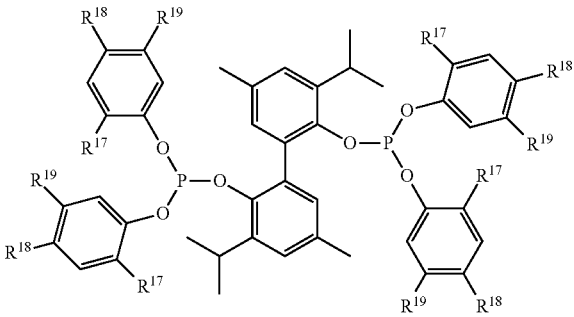

(VIII)

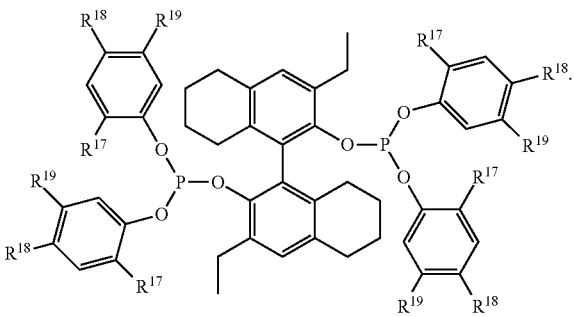

(IX)

Additional examples of bidentate phosphite ligands can include a ligand selected from a member of the group represented by Formulae (X) and (XI), in which all like reference characters have the same meaning, except as further explicitly limited:

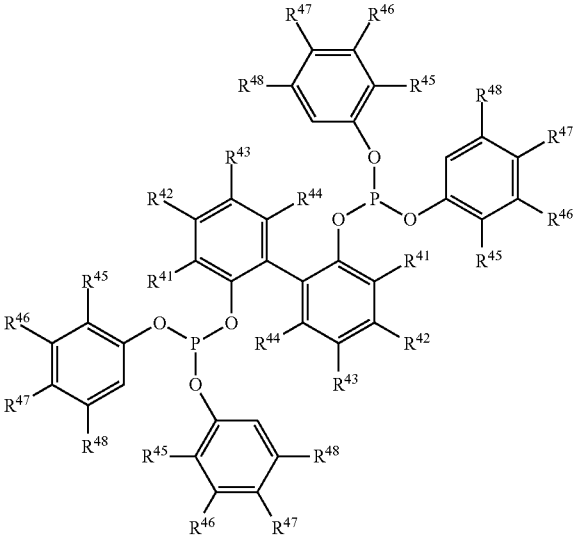

(X)

-continued

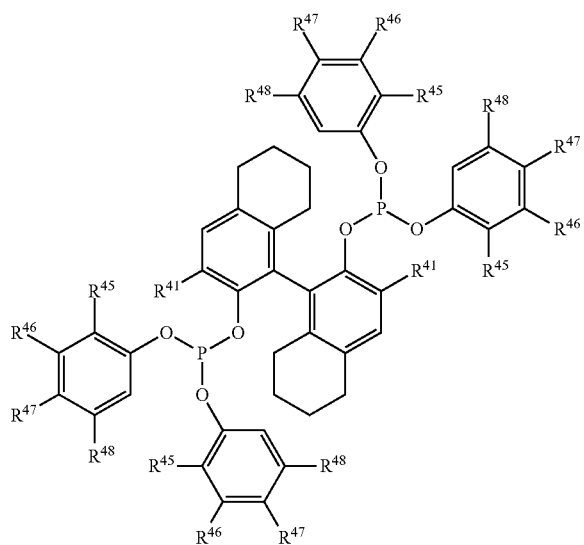

(XI)

The variables $R^{41}$ and $R^{45}$ can be independently selected from the group consisting of $C_1$ to $C_5$ hydrocarbyl, and each of $R^{42}$, $R^{43}$, $R^{44}$, $R^{46}$, $R^{47}$ and $R^{48}$ can be independently selected from the group consisting of H and $C_1$ to $C_4$ hydrocarbyl, such as alkyl or cycloalkyl.

For example, the bidentate phosphite ligand can be selected from a member of the group represented by Formula (X) and Formula (XI), wherein $R^{41}$ is methyl, ethyl, isopropyl or cyclopentyl; $R^{42}$ is H or methyl; $R^{43}$ is H or a $C_1$ to $C_4$ hydrocarbyl; $R^{44}$ is H or methyl; $R^{45}$ is methyl, ethyl or isopropyl; and $R^{46}$, $R^{47}$ and $R^{48}$ are independently selected from the group consisting of H and $C_3$ to $C_4$ hydrocarbyl.

As additional examples, the bidentate phosphite ligand can be selected from a member of the group represented by Formula (X), wherein $R^{41}$, $R^{44}$, and $R^{45}$ are methyl; $R^{42}$, $R^{46}$, $R^{47}$ and $R^{48}$ are H; and $R^{43}$ is a $C_1$ to $C_4$ hydrocarbyl. In another embodiment, $R^{41}$ is isopropyl; $R^{42}$ is H; $R^{43}$ is a $C_1$ to $C_4$ hydrocarbyl; $R^{44}$ is H or methyl; $R^{45}$ is methyl or ethyl; $R^{46}$ and $R^{48}$ are H or methyl; and $R^{47}$ is H, methyl or tertiary-butyl. In another embodiment, the bidentate phosphite ligand can be selected from a member of the group represented by Formula XI, wherein $R^{41}$ is isopropyl or cyclopentyl; $R^{45}$ is methyl or isopropyl; and $R^{46}$, $R^{47}$, and $R^{48}$ are H. The bidentate phosphite ligand can be represented by Formula (X), wherein $R^{41}$ is isopropyl; $R^{42}$, $R^{46}$, and $R^{48}$ are H; and $R^{43}$, $R^{44}$, $R^{45}$, and $R^{47}$ are methyl.

It will be recognized that Formulae (V) to (XI) are two-dimensional representations of three-dimensional molecules and that rotation about chemical bonds can occur in the molecules to give configurations differing from those shown. For example, rotation about the carbon-carbon bond between the 2- and 2'-positions of the biphenyl, octahydrobinaphthyl, and or binaphthyl bridging groups of Formulae (V) to (XI), respectively, can bring the two phosphorus atoms of each Formula in closer proximity to one another and can allow the phosphite ligand to bind to nickel in a bidentate fashion. The term "bidentate" is well known in the art and means both phosphorus atoms of the ligand are bonded to a single nickel atom. In addition, use of an optically active moiety such as sec-butyl for $R^{41}$ can result in optically active catalysts.

Method of Using Nickel-Ligand Complex.

Various embodiments provide a method that includes using a nickel-ligand complex formed from the nickel metal to catalyze one or more chemical reactions. For example, in some embodiments, a suitable embodiment of a nickel-ligand complex can be used as a catalyst for the hydrocyanation of conjugated dienes to mononitriles, or for the hydrocyanation of unsaturated nitriles to provide dinitriles (e.g., adiponitrile).

Method for Determining the Ligand-Complexation Activity of a Nickel Metal.

In various embodiments, the present invention provides a method for determining the ligand-complexation activity of a nickel metal. Determining can include predicting the relative ligand-complexation activity of a nickel metal. The method can include determining the ligand-complexation activity of the nickel metal from the concentration of sulfur as amorphous nickel sulfide in the nickel metal. For example, the method can include determining the concentration of sulfur as amorphous nickel sulfide in the nickel metal, using any one or more suitable analytical techniques, and then correlating the determined concentration of sulfur as amorphous nickel sulfide to ligand-complexation activity, wherein a higher concentration of sulfur as amorphous nickel sulfide indicates a higher ligand-complexation activity of the nickel metal.

In some embodiments, the determined ligand-complexation activity of the nickel metal is an activity relative to the ligand-complexation activity of another nickel metal having a concentration of amorphous nickel sulfide therein. In some embodiments, the ligand-complexation activity of the nickel metal correlates linearly with the concentration of sulfur as amorphous nickel sulfide.

EXAMPLES

Various embodiments of the present invention can be better understood by reference to the following Examples which are offered by way of illustration. The present invention is not limited to the Examples given herein.

General

Ligand (V) is 3,3'-diisopropyl-5,5',6,6'-tetramethyl-[1,1'-biphenyl]-2,2'-diyl tetrakis(2,4-dimethylphenyl) bis(phosphite).

To evaluate the suitability of nickel preparations for preparation of hydrocyanation catalysts, an assay was used to determine the activity based on its propensity to form soluble nickel phosphorus ligand complexes. The assay included mixing a particulate nickel metal test sample with one or more phosphorus-containing ligands and a Lewis acid in an organonitrile solvent. Unless otherwise described, the organonitrile solvent was 3-pentenenitrile, the phosphorus-containing ligand used was Ligand (V), and the Lewis acid was $ZnCl_2$.

Ligand (V)

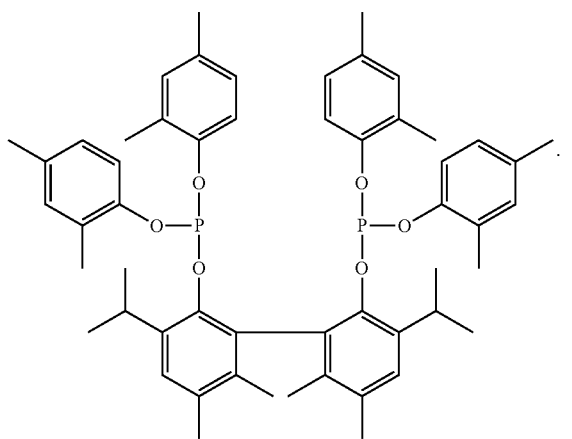

To avoid contact with air, a reactor bottle, equipped with a magnetic stir bar, was charged with the reactants inside a dry box operating with a dry nitrogen atmosphere. Sufficient agitation was used to suspend the nickel-containing solid in this reaction mixture. As the mixture was warmed to 60° C.-80° C. (e.g., 60° C.) over a period of hours, the level of solubilized nickel in solution was measured by liquid chromatography (LC) at intervals of from 5 minutes to one hour. The limit of detection for this assay was about 20-50 ppm soluble nickel in the form of soluble nickel complexes of Ligand (V). Nickel becomes soluble in the 3-pentenenitrile when it forms a complex with the phosphorus-containing ligand. A final sample can be taken after a known equilibrium concentration value of soluble nickel complex is achieved. Reaching this equilibrium concentration of soluble nickel typically takes about 2 to 24 hours based on the operating conditions. Unreacted nickel metal was removed from the mixture by filtration or centrifugation, and the samples taken for LC were filtered.

A nickel powder obtained from MetChem BNC using a one-step hydrogenation process (e.g., not including calcination pretreatment), where the hydrogenation is performed at 400° C., is described in Table 1 and has nickel activity that is typically below that which enables the efficient preparation of the nickel complexes suitable for use in a manufacturing process involving a hydrocyanation catalyst.

TABLE 1

Analysis of MetChem Basic Nickel Carbonate Powder. Nickel 47% by weight

| Cobalt 65 ppm | Copper 20 ppm | Iron 55 ppm | Zinc 12 ppm |
|---|---|---|---|
| Magnesium 60 ppm | Calcium 60 ppm | Sodium 60 ppm | Sulfur 175 ppm |

An empirical rate equation for Ni dissolution in catalyst-preparation assay was employed to provide a numerical value indicative of nickel 'activity' (ability to become a soluble catalyst complex with Ligand (V)) in the following reaction:

Ni+Ligand(V)(A)+ZnCl$_2$(B)+3PN ⇌ Catalyst(C)

The following equation describes the rate of Nickel-Ligand (V) catalyst formation:

$$r = a * k' * w_{Ni} * C_A^{a'} * C_B^{b} * [1 - C_c/(K_{eq} * C_A * C_B)] * 2 * (C_A/C_{A0})/[1+(C_A/C_{A0})]$$

where:
a=activity of nickel
$w_{Ni}$=weight loading of nickel (weight of nickel/weight of solution)
k'=Arrhenius rate constant:

[(mmoles Ni/liter)$^{\wedge}$0.5/hr]=1.539×10$^{10}$ exp[−6832.1/T(K)]

$C_A$=concentration of Ligand (V) (mmol/L)
$C_{A0}$=Initial concentration of Ligand (V) (mmol/L)
$C_B$=concentration of ZnCl$_2$ (mmol/L)
a'=order of reaction with respect to Ligand (V)=0
b=order of reaction with respect to ZnCl$_2$=0.5
$K_{eq}$=equilibrium constant for the chemical reaction

[liters/mmol]=exp[11555/T(K)−35.231]

T=temperature in degree Kelvin.

It was assumed that the 3-pentenenitrile is in far excess. The order of reaction with nickel loading is considered to be 1.

The rate constant k' was defined for a standard MetChem BNC reduced to nickel at 400° C. under pure hydrogen. However, to account for other sources of nickel that can have different properties, a factor is applied that is termed the activity of nickel dissolution. Unless specified otherwise, herein the 'activity' number was chosen to be 1 for the specific condition of MetChem BNC calcined and reduced at 400° C. to nickel, dissolved at 80° C. in the catalyst-preparation solution with ZnCl$_2$/Ligand (V) molar ratio of 0.8 and 4 wt % nickel loading where dissolution is at a rate of 980 ppm Ni/hr. In principle, a higher activity is essentially a higher rate constant specific to a given nickel. In order to move away from separately determining the rate constant for each type of nickel, the activity term was defined to get around this issue.

Using such an equation, a nickel metal preparation is active if it has an activity of at least 4.0, or at least 6.0, or at least 7.0, or at least 8.0. Nickel metal preparations are also active if they efficiently form nickel phosphorus ligand complexes at a rate suitable for use in a manufacturing process involving a hydrocyanation catalyst. A suitable rate is a time for achieving equilibrium in the formation of a nickel metal phosphorus ligand complex of no more than 8 hours, no more than 6 hours, no more than 5 hours, no more than 4 hours, no more than 3 hours, no more than 2 hours, no more than 1 hour, or no more than 30 minutes. Nickel preparations that form complexes with phosphorus-containing ligands very slowly (e.g., by requiring several days or a week for formation) are not active nickel preparations useful for generating hydrocyanation catalysts.

Note that if recrystallized Ligand (V) is employed in the assay, the measured nickel activity is higher than if an extracted (e.g., recycled) Ligand (V) preparation is employed. The difference in activity is about 2-fold.

Part I. Nickel Metal with High Ligand-Complexation Activity.

Activities shown in this Part derive from pure Ligand (V) for all lab samples.

Example 1. Decomposition of Nickel Formate—Temperature and Activity

Nickel formate from Königswarter & Ebell (a company of the TIB Chemicals group, "K&E") was completely decomposed at 200° C., 250° C., 275° C., 300° C., and 400° C. A sample of nickel formate was loaded and heated in a fixed bed reactor (Nickel Preparation Unit, "NPU") under a flow of Nitrogen (1 L/min) at a heat ramp rate of 2° C./min (slow ramp) to 20° C./min and held at the desired process temperature (200-400° C.) for as long as necessary (e.g., as dictated by the amount of evolving gases ($H_2O$, $CO_2$, CO, $H_2$) detected by an on-line gas analyzer connected to the exit of the reactor). Decomposition was considered complete when gases were no longer detected. Full decomposition, or the concentration of inert material (e.g., residues that were not dissolvable or anything other than Ni(0) metal), was confirmed and estimated in one or more of several ways, using techniques such as X-ray diffraction (XRD), oxidative thermogravimetric analysis (TGA), elemental analysis, and gravimetrically after complete chemical dissolution.

FIG. 1 illustrates a typical heat profile and the corresponding $CO/CO_2$ gas evolution as detected by the on-line gas analyzer. The reaction was essentially complete after 4 h of reaction time when heating the sample at 250° C.

Figure 2:
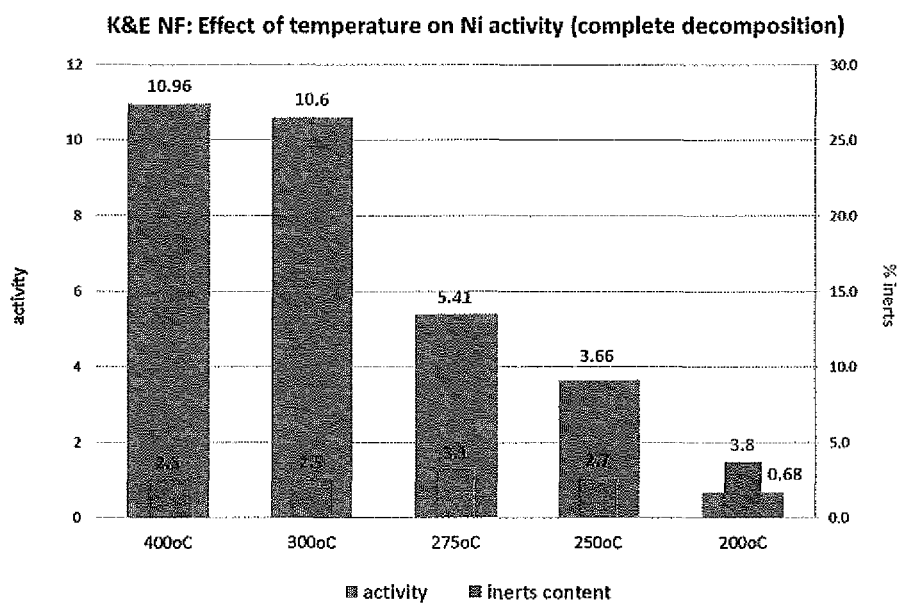
FIG. 2 illustrates the activity of various nickel metal samples formed from nickel formate at various temperatures, in accordance with various embodiments.

FIG. 2 illustrates the activity of nickel metal samples formed from the same nickel formate source at various temperatures. FIG. 2 shows that the activity increases with temperature and plateaus around about 300° C. It can be seen that the concentration of inerts was fairly constant across all temperatures tested. All nickel products had approximately the same concentration of sulfur (0.4-0.5% as measured by combustion microcoulometry/infra-red spectroscopy), so the observed activities are neither explained by the degree of decomposition of the Ni source (or the presence of inerts in the nickel) nor by the total concentration of sulfur.

Figure 3:
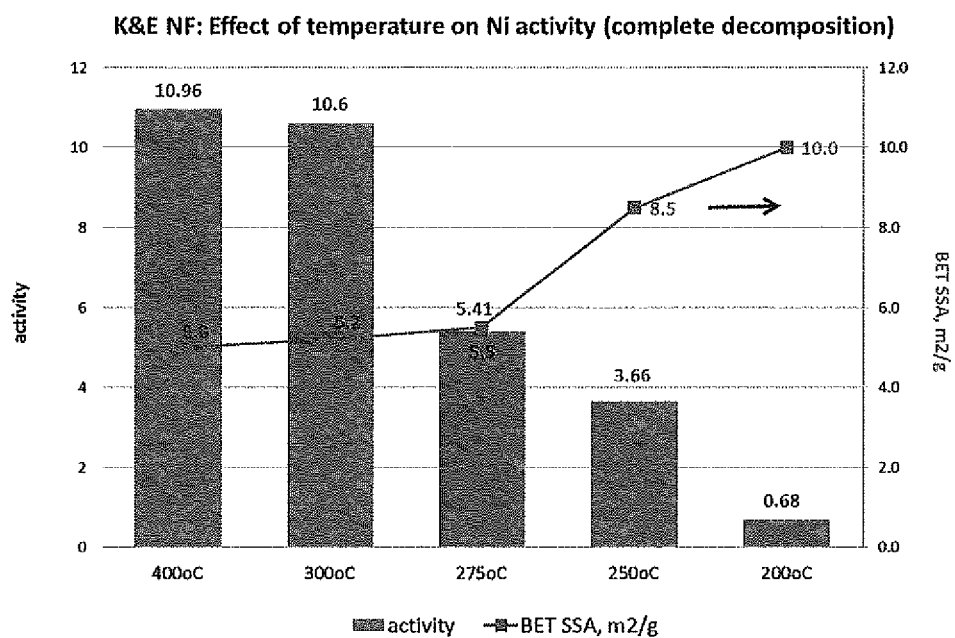
FIG. 3 illustrates the activity and surface area of the nickel metal samples formed from nickel formate at various temperatures, in accordance with various embodiments.

Example 2. Decomposition of Nickel Formate—Temperature, Surface Area, and Activity The surface area of the nickel metal samples formed in Example 1 was measured using BET. FIG. 3 illustrates the activity and surface area of the nickel metal samples formed at various temperatures. FIG. 3 shows that, surprisingly, activity was inversely proportional to surface area. The observed activities were not explained by the measured BET surface areas.

Example 3. Decomposition of Nickel Formate in the Presence of $H_2$

Figure 4:
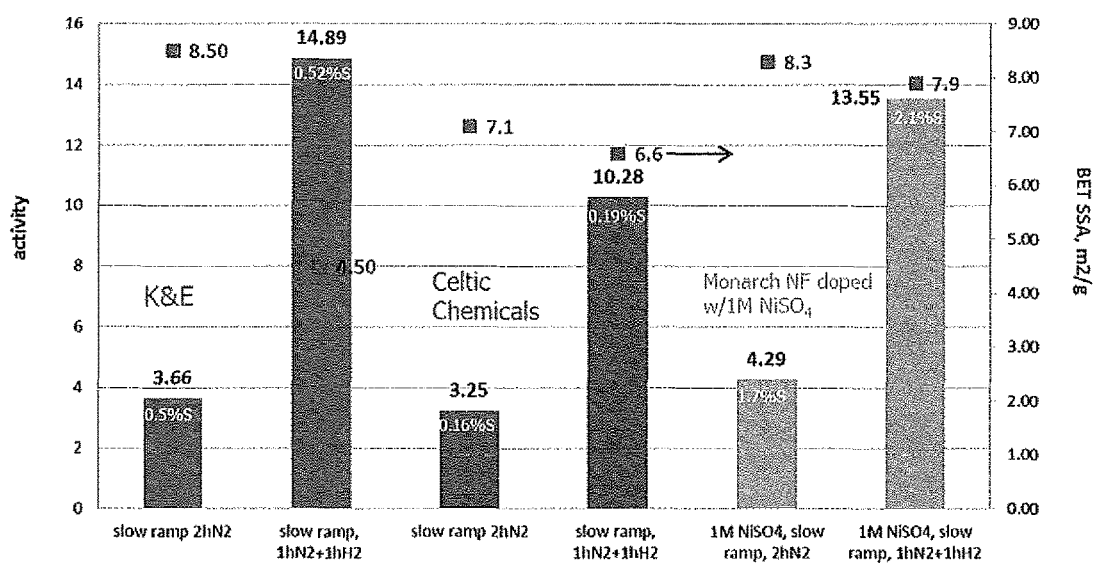
FIG. 4 illustrates activity and surface area for various nickel formate samples decomposed at 250° C. with and without an $H_2$ atmosphere, in accordance with various embodiments.

Following the procedure described in Example 1, samples of nickel formate from K&E, Celtic Chemicals, and Monarch (sulfated by wet-impregnation with a 1M $NiSO_4$ solution and dried) were decomposed at 250° C. after a slow heat ramp of 2° C./min, either for 2 h in an $N_2$ atmosphere or 1 h in an $N_2$ atmosphere followed by 1 h in an $H_2$ atmosphere (20% $H_2$ in $N_2$). The nickel formate was essentially decomposed by the time the $H_2$ atmosphere was used. FIG. 4 illustrates the activity for the nickel formate samples decomposed at 250° C. with and without the $H_2$ atmosphere. FIG. 4 shows that significant improvement in activity occurred with the use of $H_2$ in all cases. FIG. 4 also shows the BET surface areas and total sulfur concentrations measured for all of the decomposed, or decomposed and reduced, samples. The results indicate that the surface areas and total sulfur contents cannot explain the enhanced activity since a decrease in BET surface area is observed when treating the samples with $H_2$ while the total sulfur content remains fairly constant.

Figure 5:
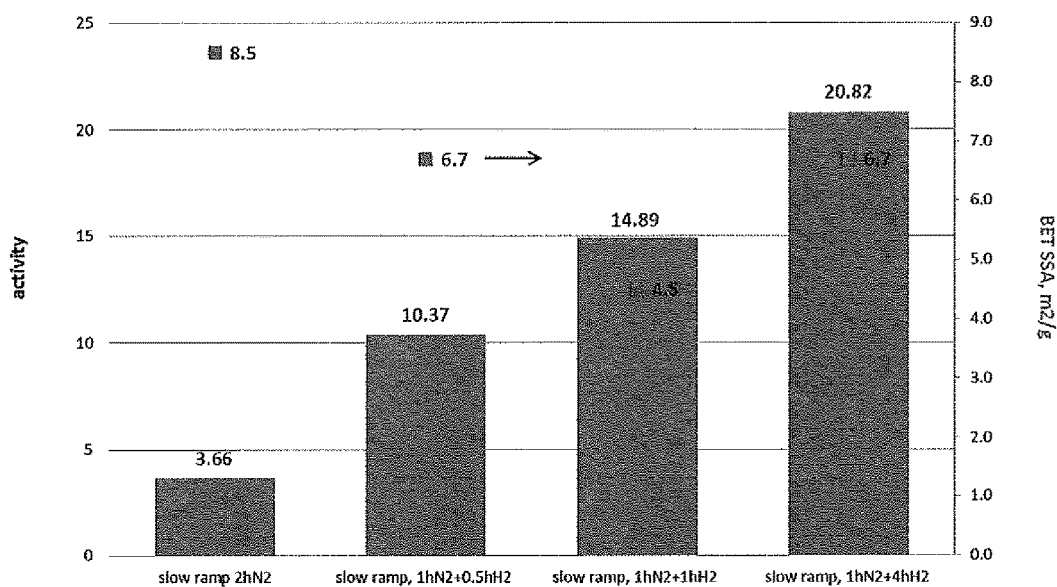
FIG. 5 illustrates activity for various nickel formate samples decomposed at 250° C. with and without an $H_2$ atmosphere, in accordance with various embodiments.

Following the procedure described in Example 1, the K&E nickel formate was also decomposed at 250° C. using a slow ramp, i.e., at a heat ramp rate of 2° C./min with 1 h $N_2$ and 0 h, 0.5 h, 1 h, or 4 h $H_2$ atmosphere of similar concentration, with the results illustrated in FIG. 5. The nickel formate was completely decomposed prior to use of the $H_2$ atmosphere. A continuous increase in activity was observed as the amount of $H_2$ supplied post-decomposition increases.

Example 4. Decomposition of Nickel Formate—Temperature and Activity

Figure 6:
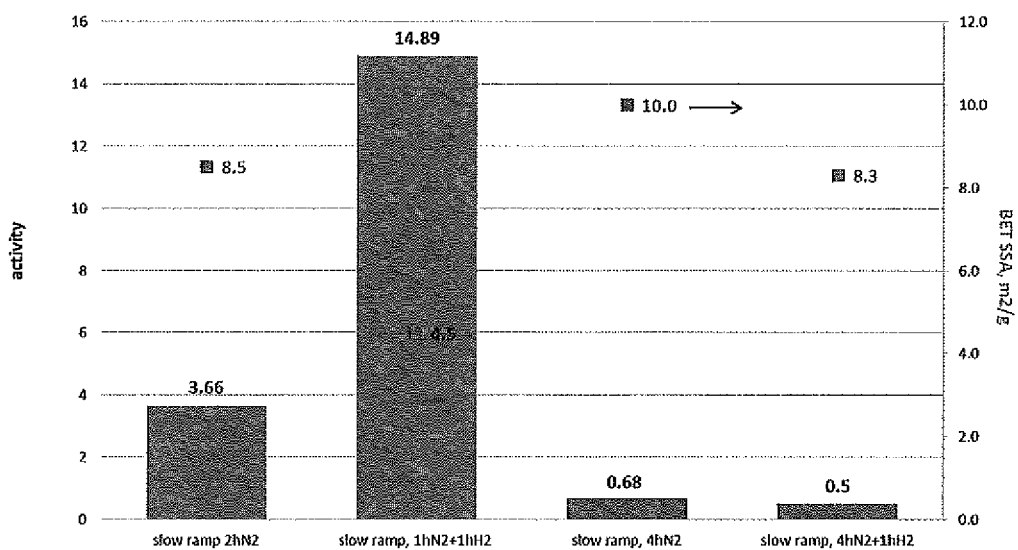
FIG. 6 illustrates activity for various nickel formate samples decomposed at 250° C. or 200° C. with and without an $H_2$ atmosphere, in accordance with various embodiments.

Using nickel formate from K&E, following the procedure described in Example 1, nickel formate was decomposed at 250° C. or 200° C., using at 250° C. either a 2 h slow ramp, i.e., at a heat ramp rate of 2° C./min in an $N_2$ atmosphere or 1 h in an $N_2$ atmosphere and 1 h in an $H_2$ atmosphere (20% in $N_2$), and at 200° C. either a 4 h slow ramp, i.e., at a heat ramp rate of 2° C./min in an $N_2$ atmosphere or 4 h in an $N_2$ atmosphere and 1 h in an $H_2$ atmosphere (20% in $N_2$). The nickel formate was essentially decomposed prior to use of the $H_2$ atmosphere. The results are illustrated in FIG. 6. The results show that regardless of the use of $H_2$, temperatures of greater than 200° C. produce far greater activity.

The overall results for nickel formate shown in FIGS. 1-6 support a hypothesis that the increase in activity is linked to a change in the chemical nature of the sulfur species present initially in the Nickel precursor. In other words, the origin of the observed activity improvement is the presence of sulfur in the form of sulfide in the nickel product and those sulfide species would play an important role in promoting Ni-ligand complex formation. Since the nickel formate starting material includes a sulfur impurity in the form of sulfate initially, the improvement in activity is due to the change in oxidation state of sulfur during processing (from sulfate to sulfide, e.g., $S^{+6}$ to $S^{-2}$), which occurs in the presence of in-situ generated $H_2$ during nickel formate decomposition or by deliberate addition of $H_2$. The results show that in all likelihood the reduction of sulfate to sulfide is very slow at 200° C., hence the observed poor activity. Substantially no reduction of sulfate occurs for nickel formate when carrying out the reduction below 250° C. The nature of the sulfur species present in the 200° C. decomposed product (e.g., as being essentially in the form of sulfate), was confirmed via the analytical techniques described herein in the Examples of Part II.

Example 5. Activities of Products Derived from Sulfur-Doped Starting Materials

Several basic nickel carbonate and nickel oxide starting materials were doped with various inorganic sulfur sources of different sulfur oxidation states including nickel sulfate (+6), sodium sulfate (+6), sodium sulfite (+4), sodium thiosulfate (+6 and −2), cyclooctasulfur i.e elemental sulfur (0) and metal sulfides, $Na_2S$, $Ni_3S_2$ and $Co_6S_5$ (−2). As used in this Part, "undoped" means no additional sulfur has been introduced beside the residual sulfur (e.g., sulphate impurity) already present in the precursor.

The BNC was either mixed with an aqueous solution of the inorganic sulfur source, filtered and dried in an oven, or physically mixed with elemental sulfur or metal sulfide., prior to high-temperature processing. Calcination and/or reduction of BNC/NiO were performed using the same reactor as for nickel formate. Calcination was carried out under $N_2$ for 2 h at 400° C. while reduction of NiO was performed in 20% $H_2/N_2$ for 2 h at 300° C. or 400° C. The activities of the product were measured, with the results illustrated in Table 2.

Table 2 shows that alternative forms of sulfur of different oxidation states in the starting material can be used to make active Ni products but as seen previously with nickel formate, a reducible sulfur source is present when producing an active nickel material. The experiments involving sodium sulfate as the dopant show poor activity improvements compared to the baseline activities (undoped Ni precursors) due to the poor conversion of sodium sulfate to sulfide under the conditions used.

X-ray absorption near edge structure (XANES) and X-ray photoelectron spectroscopy (XPS) analyses have been performed to validate the inorganic analytical techniques and the nature of the sulfur species present in the Ni samples. A methylene blue spectrophotometric analytical technique was also used to confirm the presence of S as sulfide in Ni samples.

The making of the particulate Ni products covered a wide range of conditions such as the use of different sulfur

TABLE 2

Activities of nickel products derived from starting materials containing various sulfur-sources.

| Precursor | Average Sulfur Oxidation State in Ni precursor | Sulfur form/doping | T° C. (calc/red) | BET SSA, (m²/g) | % S | % $S^{2-}$ | activity |
|---|---|---|---|---|---|---|---|
| MetChem BNC | +6 | No doping (as received) | 400/300 | — | 0.02 | <0.02 | <1[a] |
| MetChem BNC | 0 | 1% $S_8$ based on Ni | 400/300 | 17.1 | 1.23 | 1.16 | 19.7 |
| MetChem BNC | +2 | 0.5M $Na_2S_2O_3$ | 400/300 | 14 | 2.81 | 1.66 | 19.0 |
| MetChem BNC | +4 | 0.5M $Na_2SO_3$ | 400/300 | 14.8 | 3.48 | 1.19 | 19.3 |
| MetChem BNC | +6 | 1M $NiSO_4$ | 400/400 | 6.6 | 1.21 | 1.17 | 10.1 |
| Umicore BNC | +6 | No doping (as received) | 400/400 | 10 | 0.07 | <0.07 | 0.4 |
| Umicore BNC | +6 | 1M $Na_2SO_4$ | 400/400 | 5.3 | 6.3 | <0.06 | 2.8 |
| Umicore BNC | +6 | 1M $NiSO_4$ | 400/400 | 12.9 | 6.60 | 5.74 | 19.5 |
| Umicore BNC | −2 | 3% $Ni_3S_2$ | 400/400 | 10.2 | 2.10 | 1.73 | 20.9 |
| Umicore BNC | −2 | 2.8% $Co_6S_5$ | 400/400 | 14.1 | 2.0 | 1.98 | 20.2 |
| MMP-NiO | +6 | No doping (as received) | —/350 | 5.5 | 0.06 | <0.06 | 3.9 |
| MMP-NiO | +6 | 0.5M $Na_2SO_4$ | —/300 | 5.5 | 0.29 | 0.07 | 3.9 |
| MMP-NiO | −2 | 0.5M $Na_2S$ | —/300 | 25.5 | 0.14 | 0.11 | 6.2 |
| MMP-NiO | 0 | 1% $S_8$ based on Ni | —/350 | 8 | 4.30 | 3.94 | 16.8 |
| Umicore Black NiO | — | No doping (as received) | 400/400 | 10.2 | 0.01 | 0.01 | <0.5 |
| Umicore Black NiO | +6 | 1M $NiSO_4$ | 400/400 | 11.2 | 8.0 | 7.7 | 6.7 |

Part II. Prediction of Nickel Metal Ligand-Complexation Activity

For this Part, total sulfur, sulfide and amorphous sulfide contents have been determined using a range of analytical techniques for Ni samples obtained by processing multiple sulfur-doped or "undoped" Ni precursors. A total of 65 Ni samples prepared in the lab and produced during scale-up trials at Procedyne Corporation have been analysed. Nickel precursors included BNC, NiO and Nickel formate dihydrate. Forms of doping include $NiSO_4$ wet impregnation, elemental sulfur, $H_2S$ and $Ni_3S_2$. As used in this Part, "undoped" means no additional sulfur has been introduced beside the residual sulfur (e.g., sulfate impurity) already present in the precursor. The analytical techniques include X-ray diffraction spectroscopy (XRD) for crystalline $Ni_3S_2$ content determination, combustion microcoulometry/IR for total sulfur content and inductively coupled plasma optical emission spectroscopy (ICP-OES) for sulfate content determination after removal of sulfides by HCl-digestion of the Nickel samples in Nitrogen-atmosphere. Sulfide content was calculated as total sulfur content minus sulfur content as sulfate. Total content of sulfur as amorphous $NiS_x$ was calculated as total sulfide content minus total content of sulfide as crystalline $Ni_3S_2$, where total S content as crystalline $Ni_3S_2$ equals the concentration of crystalline $Ni_3S_2$ measured by XRD multiplied by the Molecular Weight of Sulfur times two, divided by the Molecular Weight of $Ni_3S_2$.

sources, process type, temperature (from 190° C. to 400° C.), $H_2$ concentration, $H_2$ hold-up time, ramp rate (2-20° C./min), steam concentration (10-30%), and the like. This allowed variation of the reactivity and fate of the sulfur species initially present in the Ni precursors, hence the oxidation state of S and its form (amorphous $NiS_x$ or crystalline $Ni_3S_2$). Activities shown in this Part derive from pure Ligand (V) for all lab samples. Further tests have been conducted to predict reactivity and fate of sulfur species during processing using temperature-programmed reaction mass spectroscopy (TPR-MS) and temperature-programmed reaction X-ray spectroscopy (TPR-XRD) techniques Example 6. Activity of Nickel Metal Samples and Sulfur Content Thereof FIG. 7 illustrates the activity of the nickel metal samples versus the total sulfur content in PPMW for samples produced under various conditions.

Figure 7:
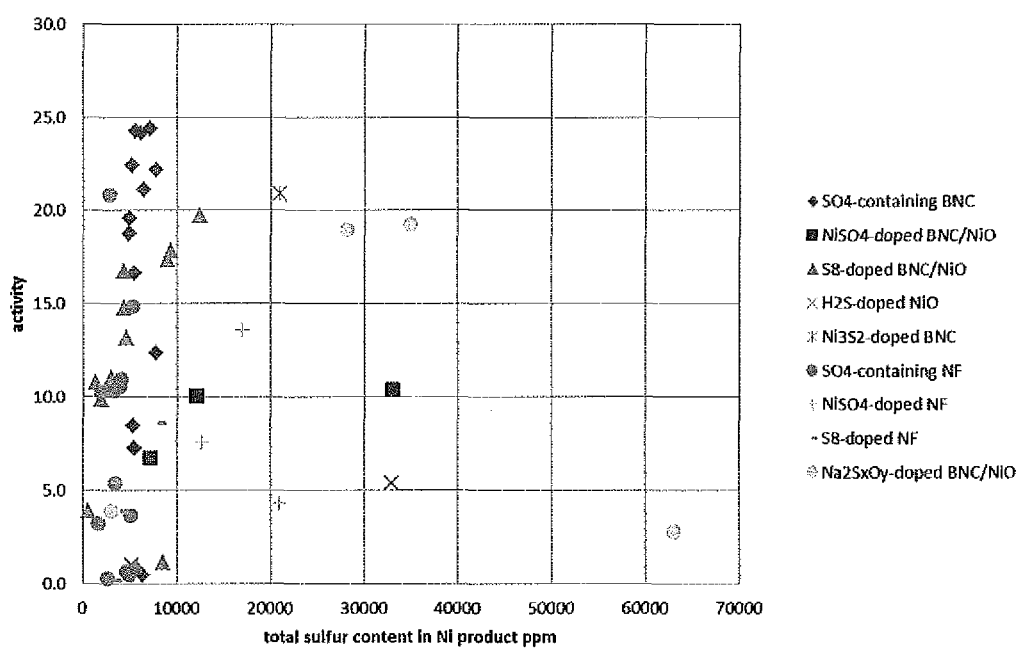
FIG. 7 illustrates the activity of the nickel metal samples versus the total sulfur content for samples produced under various conditions, in accordance with various embodiments.
Figure 8:
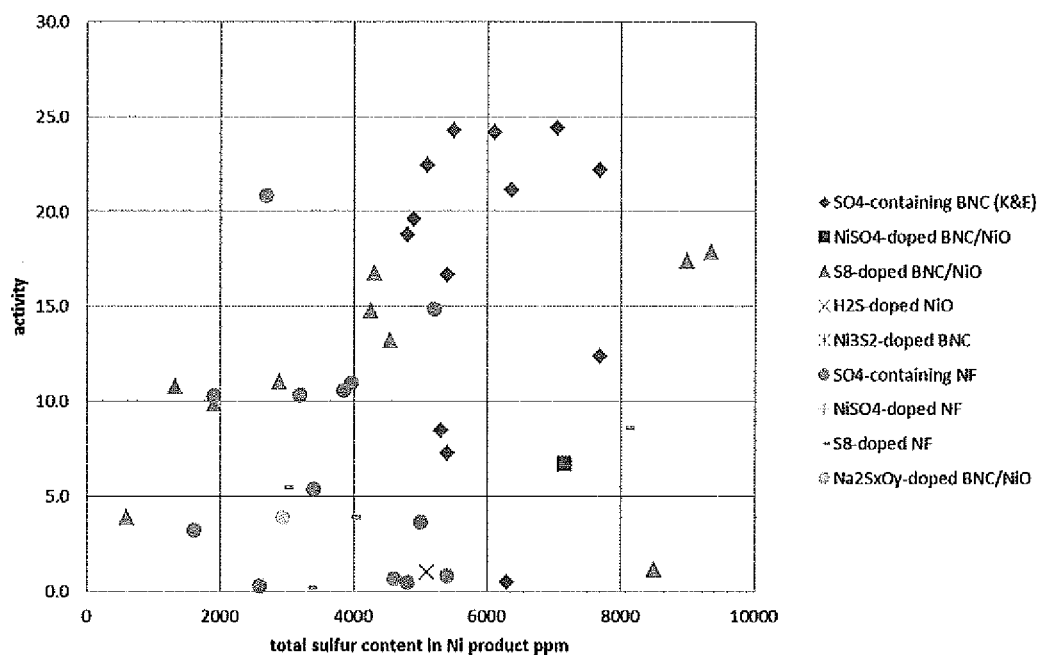
FIG. 8 illustrates the activity of the nickel metal samples versus the total sulfur content for samples produced under various conditions, where S content is less than 1%, in accordance with various embodiments.

FIG. 8 is a close-up of the 0-10,000 ppmw section of FIG. 7.

Example 7. Activity of Nickel Metal Samples and Sulfide Content Thereof

Figure 9:
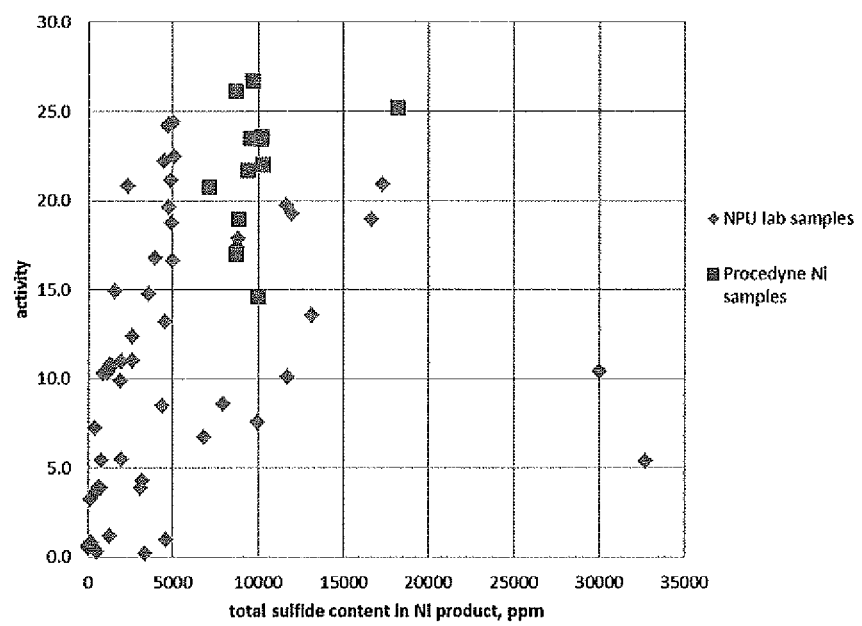
FIG. 9 illustrates the activity of the nickel metal samples versus the total sulfide content for samples produced under various conditions, in accordance with various embodiments.
Figure 10:
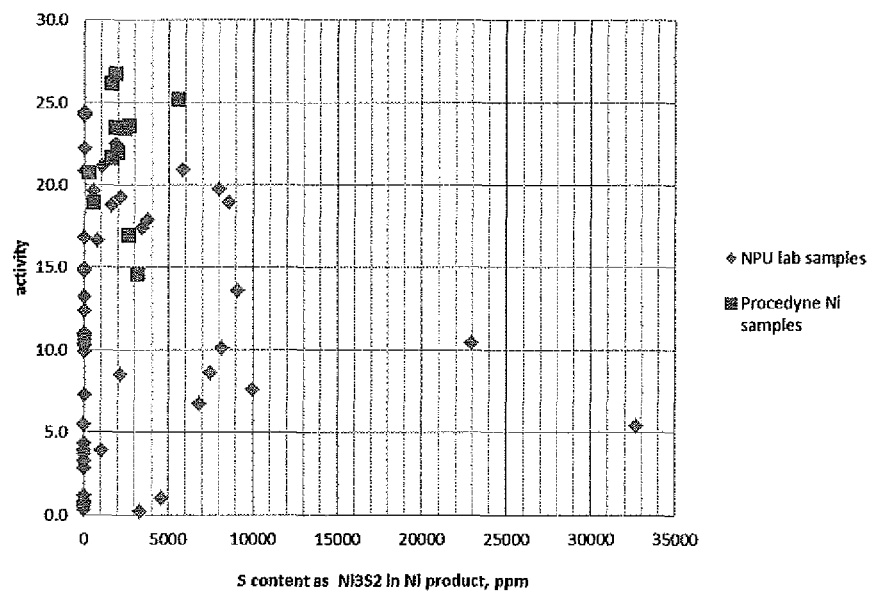
FIG. 10 illustrates the activity of the nickel metal samples versus the total sulfur content as crystalline $Ni_3S_2$ for samples produced under various conditions, in accordance with various embodiments.

FIG. 9 illustrates the activity of the nickel metal samples versus the total sulfide content for samples produced under various conditions, calculated as $[S^{2-}]_{ppm}=[\text{total S}]_{ppm}-[\text{S as SO}_4^{2-}]_{ppm}$. In FIGS. 9-14, all of the samples from FIGS. 7-8 are shown as blue, and commercial samples from Procedyne are shown as red. FIGS. 9, 10, and 14 include Procedyne samples, the activity of which were determined differently (using extracted ligand mixture as opposed to pure ligand V). A factor 2 has therefore been applied to the Procedyne Ni activities to put all activities on the same basis (as if pure D80 had been used).

FIG. 10 illustrates the activity of the nickel metal samples versus the total sulfur content as crystalline $Ni_3S_2$ (as measured by XRD) for samples produced under various conditions, calculated as $[\text{total S content as crystalline } Ni_3S_2]_{ppm}=[Ni_3S_2]_{ppm}*2*MW_S/MW_{Ni3S2}=0.267*[Ni_3S_2]_{ppm}$.

Figure 11:
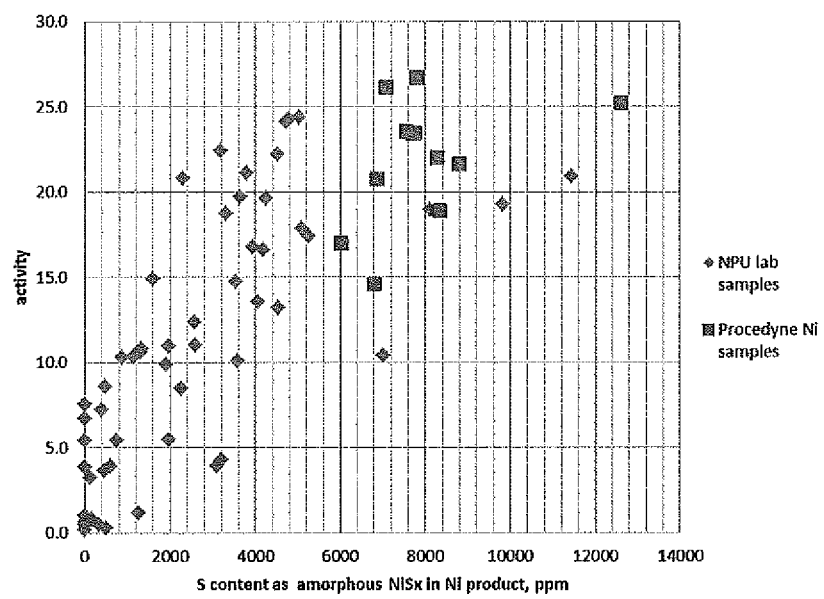
FIG. 11 illustrates the activity of the nickel metal samples versus the total sulfur content as amorphous $NiS_x$ for samples produced under various conditions, in accordance with various embodiments.

Example 8. Activity of Nickel Metal Samples and Amorphous $NiS_x$ Content Thereof FIG. 11 illustrates the activity of the nickel metal samples versus the total sulfur content as amorphous $NiS_x$ for samples produced under various conditions, calculated as $[S^{-2}\text{ as amorphous } NiS_x]_{ppm}=[S^{2-}]_{ppm}-[S^{2-}\text{ as crystalline } Ni_3S_2]_{ppm}$. For all of the calculations in this Example, 0.54% S was assumed for all Ni products made from the same lot of K&E BNC and 0.45% S for all Ni products made from the same lot of K&E nickel formate.

Figure 12:
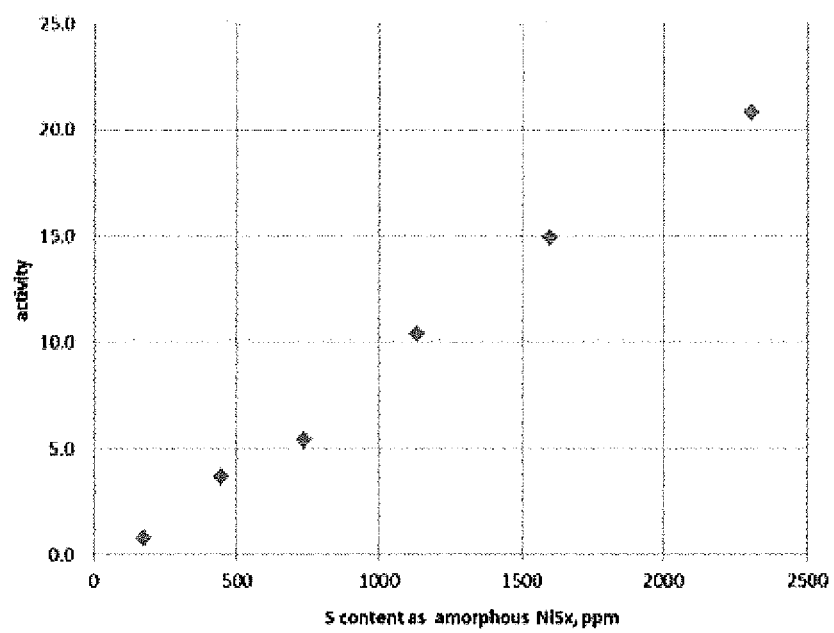
FIG. 12 illustrates the activity of the nickel metal samples versus the total sulfur content as amorphous $NiS_x$, in accordance with various embodiments.

FIG. 12 illustrates the activity of the nickel metal samples versus the total sulfur content as amorphous $NiS_x$ for samples produced from sulfate-containing (undoped) K&E nickel formate processed at 250° C.

Figure 13:
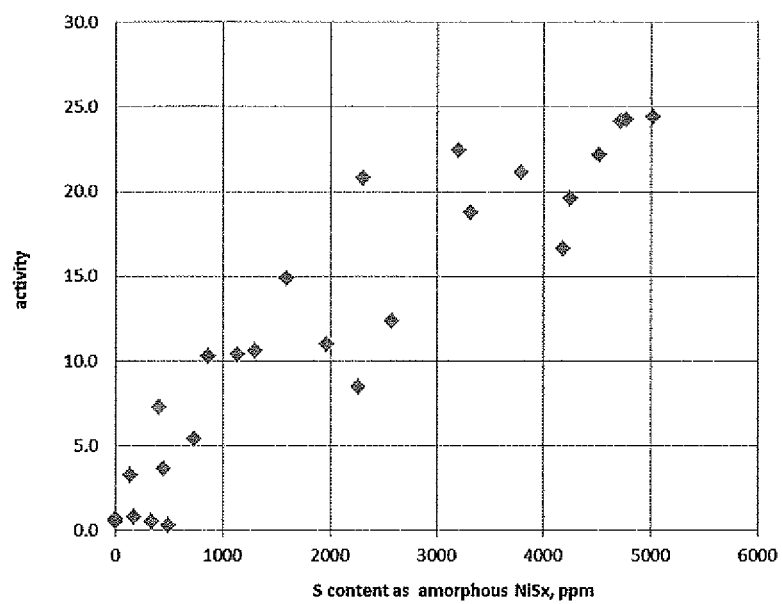
FIG. 13 illustrates the activity of various nickel metal samples versus the total sulfur content as amorphous $NiS_x$, in accordance with various embodiments.
Figure 14:
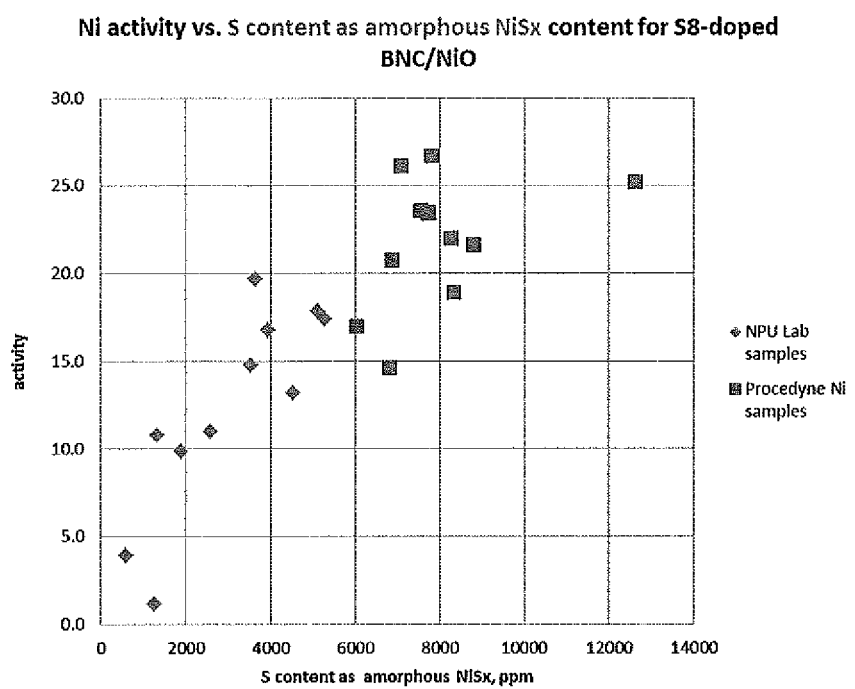
FIG. 14 illustrates the activity of various nickel metal samples versus the total sulfur content as amorphous $NiS_x$, in accordance with various embodiments.

FIG. 13 illustrates the activity of various nickel metal samples versus the total sulfur content as amorphous $NiS_x$ for samples produced from sulfate-containing (undoped) Ni precursors (BNC/NiO/nickel formate).

FIG. 14 illustrates the activity of the nickel metal samples versus the total sulfur content as amorphous $NiS_x$ for samples produced from elemental sulfur-doped BNC/NiO.

Example 9. TPR-MS (NiO, BNC)

Figure 15:
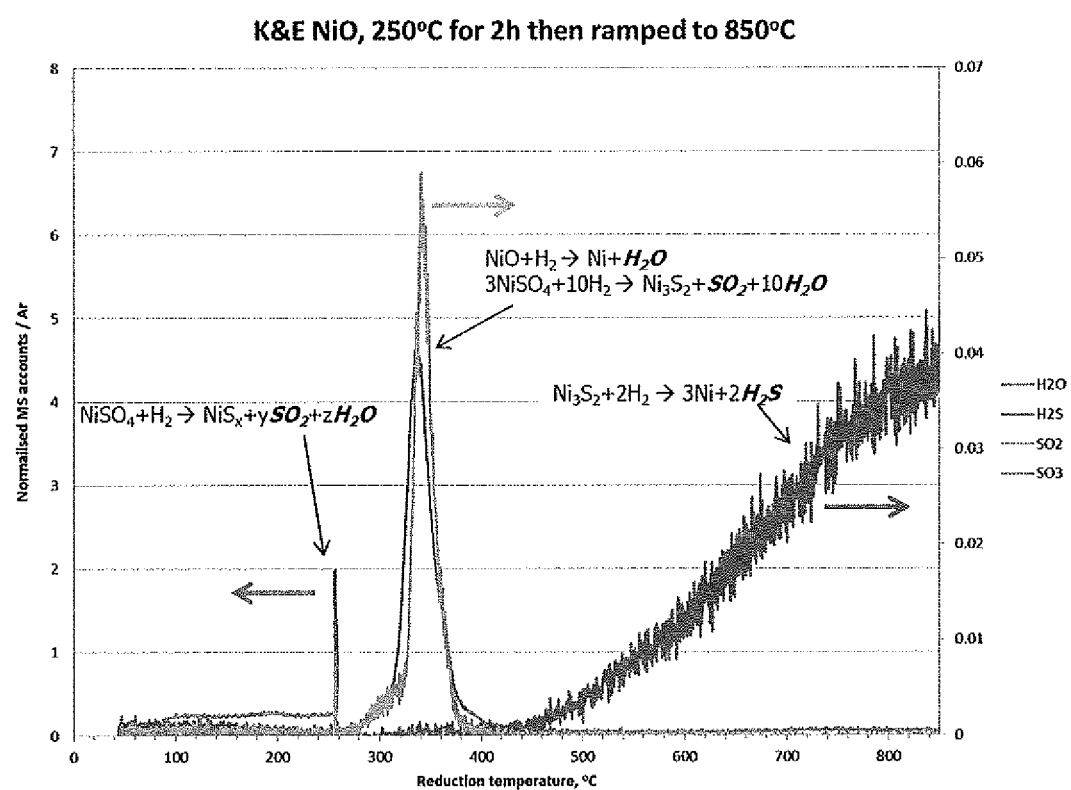
FIG. 15 illustrates a TPR-MS of a preparation of a nickel metal sample from a NiO sample containing sulfur as sulfate, in accordance with various embodiments.

FIG. 15 illustrates a TPR-MS of a preparation of a nickel metal sample from K&E NiO containing a sulfate impurity, heated at a rate of 10° C./min and held at 250° C. for 2 h then ramped up to 850° C. in an $H_2$ atmosphere (10% in Argon). Despite being a semi-quantitative technique, the TPR study shows evidence of nickel sulfide formation based on the co-evolution of $SO_2$ and $H_2O$ at about 250° C., and a further increase in temperature results in the production of higher amounts of $H_2O$ and $SO_2$ until all NiO and sulfate are fully reduced at about 400° C. during the heat ramp. Further evidence of $Ni_3S_2$ formation and subsequent reduction of $Ni_3S_2$ to Ni metal is provided by the detection of $H_2S$ gas at temperatures above 450° C. These results coincide well with the analysis of the same precursor by XRD shown herein. The onset temperature of NiO reduction and $Ni_3S_2$ formation (or $NiS_x$ crystallization) is seen just above 250° C.

Figure 16:
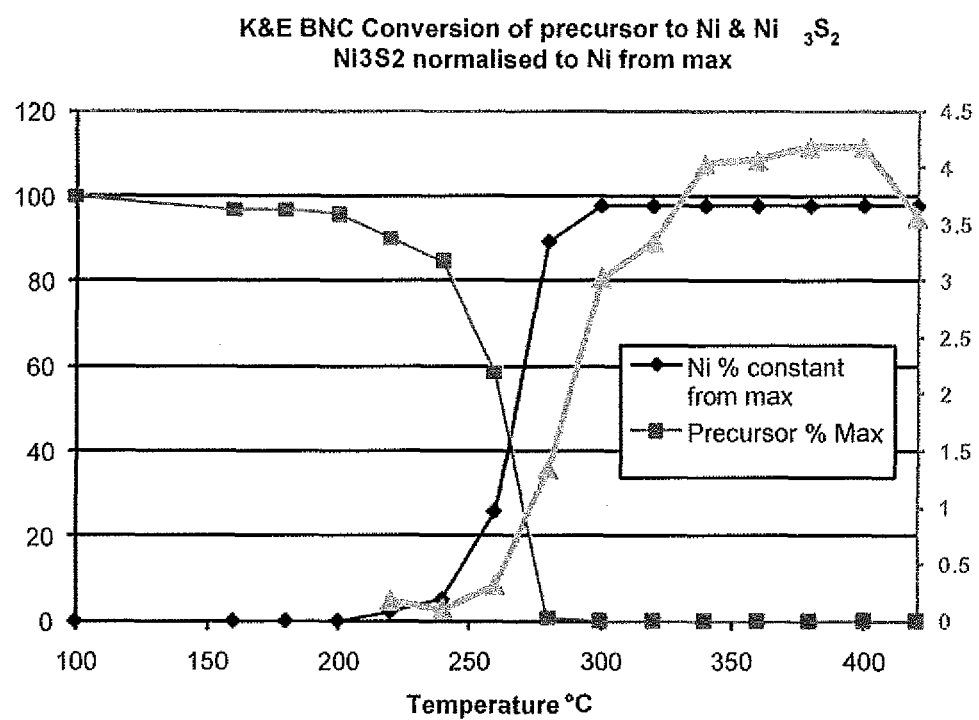
FIG. 16 illustrates a TPR-XRD of a preparation of a nickel metal sample from a BNC sample containing sulfur as sulfate, in accordance with various embodiments.

FIG. 16 illustrates a TPR-XRD of a preparation of a nickel metal sample from K&E BNC, with the $Ni_3S_2$ concentration (secondary axis) normalized to Ni from max (e.g., adjusted to make a total of 100% crystal phases).

Figure 17:
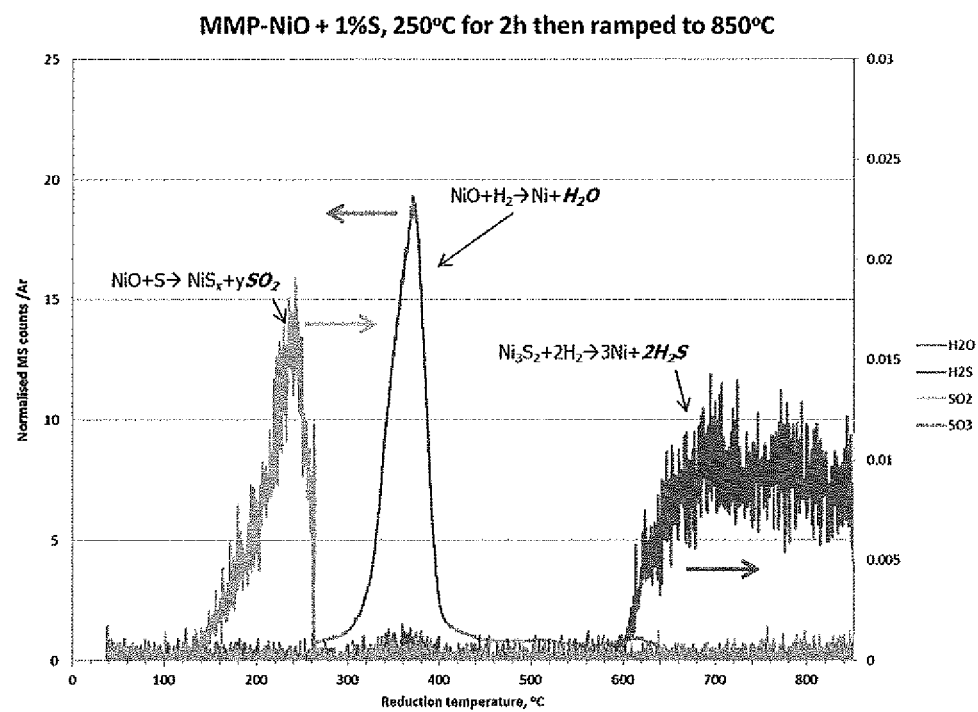
FIG. 17 illustrates a TPR-MS of a preparation of a nickel metal sample from an elemental sulfur-doped NiO sample, in accordance with various embodiments.

FIG. 17 illustrates a TPR-MS of a preparation of a nickel metal sample from a MMP-NiO sample doped with 1% elemental sulfur based on nickel, heated at a rate of 10° C./min and held at 250° C. for 2 h then ramped to 850° C. in $H_2$ atmosphere (10% $H_2$ in Argon). FIG. 17 shows evidence of sulfidation of NiO between 100° C. and 250° C. (during the heat ramp) based on the observed $SO_2$ gas evolution. No further $SO_2$ evolution is observed during heating of the sample under $H_2$ above 250° C. while NiO starts reducing above 250° C. Further evidence of $Ni_3S_2$ formation and subsequent reduction of $Ni_3S_2$ to Ni metal is provided by the detection of $H_2S$ gas at temperatures above 450° C. As seen previously in the case of the sulfate-containing BNC, the TPR-MS results shown in FIG. 17 confirm both the reduction of NiO to Ni and the formation of $Ni_3S_2$ (crystallization of $NiS_x$) above 250° C.

Figure 18:
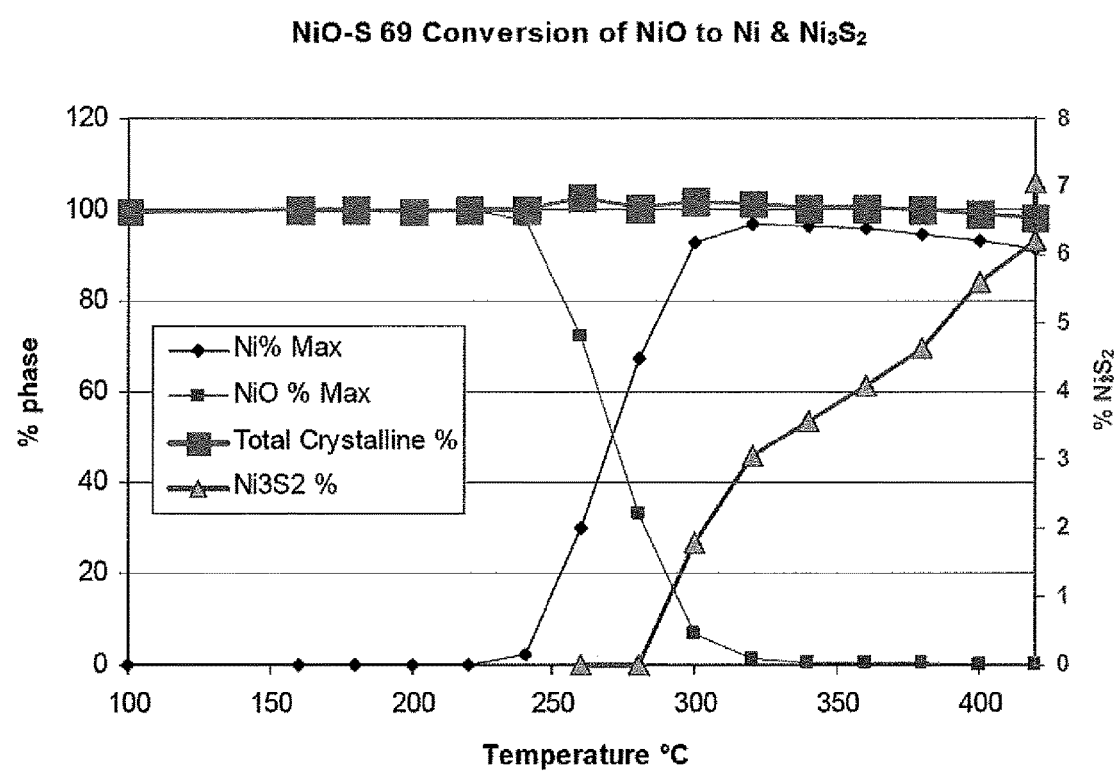
FIG. 18 illustrates a TPR-XRD of a preparation of a nickel metal sample from an elemental sulfur-doped BNC, in accordance with various embodiments.

FIG. 18 illustrates a TPR-XRD of a preparation of a nickel metal sample from MetChem BNC mixed with 1% S calcined in air at 400° C.

The terms and expressions that have been employed are used as terms of description and not of limitation, and there is no intention in the use of such terms and expressions of excluding any equivalents of the features shown and described or portions thereof, but it is recognized that various modifications are possible within the scope of the embodiments of the present invention. Thus, it should be understood that although the present invention has been specifically disclosed by specific embodiments and optional features, modification and variation of the concepts herein disclosed may be resorted to by those of ordinary skill in the art, and that such modifications and variations are considered to be within the scope of embodiments of the present invention.

Additional Embodiments

The following exemplary embodiments are provided, the numbering of which is not to be construed as designating levels of importance:

Embodiment 1 provides a method improving the reactivity of nickel for complexation with a diphosphite ligand, the method comprising:

contacting a nickel starting material with a reductant under conditions sufficient to generate a nickel-containing complexation precursor having at least about 1,500 ppmw sulfur in the form of sulfide.

Embodiment 2 provides the method of Embodiment 1, wherein the contacting comprises maintaining a temperature of about 200° C. to about 350° C.

Embodiment 3 provides the method of any one of Embodiments 1-2, wherein the contacting comprises maintaining a temperature of about 250° C. to about 300° C.

Embodiment 4 provides the method of any one of Embodiments 1-3, wherein the sulfide is amorphous $NiS_x$.

Embodiment 5 provides the method of any one of Embodiments 1-4, wherein the sulfur content of the nickel-containing complexation precursor as sulfide is about 1,500 ppmw to about 500,000 ppmw.

Embodiment 6 provides the method of any one of Embodiments 1-5, wherein the reductant comprises at least one of hydrogen, ammonia, carbon, and carbon-containing compounds.

Embodiment 7 provides the method of any one of Embodiments 1-6, wherein the reductant comprises hydrogen.

Embodiment 8 provides the method of any one of Embodiments 1-7, wherein the nickel starting material comprises at least one of basic nickel carbonate, nickel oxide, nickel carbonate, nickel bicarbonate, nickel oxalate, nickel formate, nickel squarate, nickel hydroxide, nickel nitrate, nickel cyanate, nickel sulfate, amorphous $NiS_x$ and crystalline $Ni_3S_2$.

Embodiment 9 provides the method of any one of Embodiments 1-8, wherein the nickel starting material comprises nickel formate.

Embodiment 10 provides the method of any one of Embodiments 1-9, wherein the nickel starting material comprises a reducible sulfur source.

Embodiment 11 provides the method of any one of Embodiments 1-10, wherein the nickel-containing complexation precursor has at least one property selected from the group consisting of:

BET Specific Surface Area/C50 ratio of not less than $0.07 \times 10^9$ m/gm;

at least 10% of nickel crystallites have a size (C10) that is less than about 20 nm;

nickel crystallites have an average crystallite size of no greater than about 30 nm; and/or nickel crystallite size distribution span is greater than about 1.0;

nickel-containing complexation precursor on average has at least about $10^{15}$ surface crystallites per gram of nickel;

nickel-containing complexation precursor has a BET Specific Surface Area of at least about 1 m$^2$/gm;

at least 10% of the particles of the form have a size (D10) of no greater than about 6 μm;

the nickel-containing complexation precursor has a Laser Diffraction Specific Surface Area of at least about 0.4 m$^2$/gm;

the nickel-containing complexation precursor has a BET Specific Surface Area to D10 ratio of about $0.3 \times 10^6$ m/gm to about $10.0 \times 10^6$ m/gm;

on average there are at least about $10^{31}$ surface crystallites per gram nickel that are smaller than or equal to size C10;

an equilibrium concentration of 1000-6000 ppm of soluble Ni as Ni-Ligand (V) complex is typically reached when 1-5 wt % of the nickel-containing complexation precursor is mixed with 3-pentenenitrile containing approximately 5-10 wt % Ligand (V) and 03-1.5% ZnCl$_2$ at a reaction temperature of 40-80° C.; wherein Ligand (V) has the following formula:

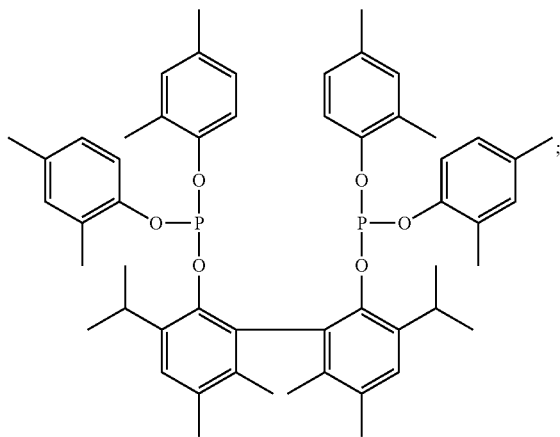

and any combination thereof.

Embodiment 12 provides the method of any one of Embodiments 1-11, further comprising, during the contacting with the reductant, contacting the nickel starting material with a sulfur source that is different than the nickel starting material.

Embodiment 13 provides the method of any one of Embodiments 1-12, further comprising calcining the nickel starting material prior to the contacting with the reductant.

Embodiment 14 provides the method of any one of Embodiments 1-13, further comprising precipitating the nickel starting material prior to the contacting with the reductant.

Embodiment 15 provides the method of any one of Embodiments 1-14, wherein the reducing further comprises contacting the nickel starting material with steam.

Embodiment 16 provides the method of any one of Embodiments 1-15, further comprising rotating or turning the nickel starting material during the contacting with the reductant.

Embodiment 17 provides the method of any one of Embodiments 1-16, further comprising forming a complex between nickel atoms of the nickel-containing complexation precursor and one or more phosphorus-containing ligands.

Embodiment 18 provides a nickel-containing complexation precursor comprising about 1,500 ppmw to about 500,000 ppmw sulfur as nickel sulfide.

Embodiment 19 provides the nickel-containing complexation precursor of Embodiment 18, wherein the nickel sulfide is amorphous NiS$_x$.

Embodiment 20 provides a method for determining the ligand-complexation activity of a nickel-containing complexation precursor, the method comprising:

determining the ligand-complexation activity of the nickel-containing complexation precursor from the concentration of sulfur as amorphous nickel sulfide in the nickel metal, wherein a higher concentration of sulfur as amorphous nickel sulfide indicates a higher ligand-complexation activity of the nickel metal.

Embodiment 21 provides a method for making a complex comprising nickel and a phosphorus-containing ligand, said method comprising contacting nickel metal containing from 1,500 to 500,000 ppmw of nickel sulfide with Ligand (V) as defined herein. In exemplary embodiment 22, the nickel sulfide is amorphous.

Exemplary embodiment 23 provides a complex comprising Ligand (V) as defined herein with a nickel metal comprising from 1,500 ppmw to 500,000 ppmw sulfide.

What is claimed is:

1. A method of improving the reactivity of nickel for complexation with a diphosphate ligand, the method comprising:
   contacting a nickel starting material comprising a reducible sulfur source with a reductant under conditions sufficient to generate a nickel-containing complexation precursor having at least about 1,500 ppmw sulfur in the form of amorphous nickel sulfide (NiS$_x$), the contacting comprising maintaining a temperature of about 200° C. to about 350° C.

2. The method of claim 1, wherein the contacting comprises staying below a temperature of about 350° C.

3. The method of claim 1, wherein the contacting comprises maintaining a temperature of about 250° C. to about 300° C.

4. The method of claim 1, wherein the contacting comprises staying below a temperature of about 300° C.

5. The method of claim 1, wherein the sulfur content of the nickel-containing complexation precursor as amorphous nickel sulfide is about 1,500 ppmw to about 500,000 ppmw.

6. The method of claim 1, wherein the reductant comprises at least one of hydrogen, ammonia, carbon, a formate ester or salt, and carbon-containing compounds.

7. The method of claim 1, wherein the reductant comprises hydrogen.

8. The method of claim 1, wherein the nickel starting material comprises at least one of basic nickel carbonate, nickel oxide, nickel carbonate, nickel bicarbonate, nickel oxalate, nickel formate, nickel squarate, nickel hydroxide, nickel nitrate, nickel cyanate, nickel sulfate, amorphous $NiS_x$, and crystalline $Ni_3S_2$.

9. The method of claim 1, wherein the nickel starting material comprises nickel formate.

10. The method of claim 1, wherein the reducible sulfur source is chosen from $NiSO_4$, $Na_2SO_3$, $NaS_2O_3$, elemental sulfur, and combinations thereof.

11. The method of claim 1, wherein the nickel-containing complexation precursor meets at least one of the following measurements:
the nickel-containing complexation precursor has a BET Specific Surface Area/C50 ratio of not less than $0.07 \times 10^9$ m/gm;
at least 10%⁰ of the nickel crystallites have a size (C10) that is less than about 20 nm;
the nickel crystallites have an average crystallite size of no greater than about 30 nm; and/or
the nickel crystallite size distribution span is greater than about 1.0;
the nickel metal on average has at least about $10^{15}$ surface crystallites per gram of nickel;
the nickel metal has a BET Specific Surface Area of at least about 1 m²/gm;
at least 10% of the particles of the form have a size (D10) of no greater than about 6 μm;
the nickel-containing complexation precursor has a Laser Diffraction Specific Surface Area of at least about 0.4 m²/gm;
the nickel-containing complexation precursor has a BET Specific Surface Area to D10 ratio of about $0.3 \times 10^6$ μm/gm to about $10.0 \times 10^6$ m/gm;
on average there are at least about $10^{31}$ surface crystallites per gram nickel that are smaller than or equal to size C10; and
an equilibrium concentration of 1000-6000 ppm of soluble Ni as Ni-Ligand (V) complex is typically reached when 1-5 wt % of the nickel-containing complexation precursor is mixed with 3-pentenenitrile containing approximately 5-10 wt % Ligand (V) and 0.3-1.5% $ZnCl_2$ at a reaction temperature of 40-80° C.; wherein Ligand (V) has the following formula:

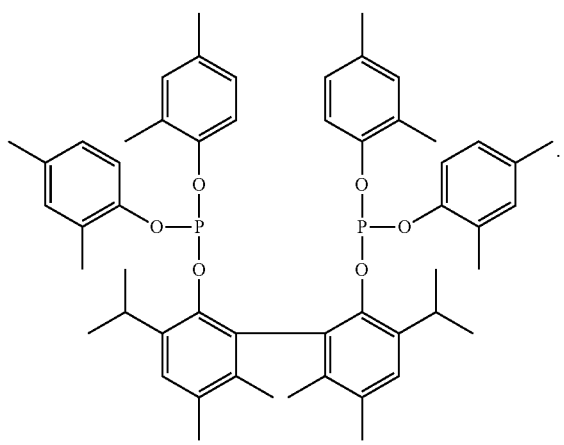

12. The method of claim 1, further comprising, during the contacting with the reductant, contacting the nickel starting material with a sulfur source that is different than the nickel starting material.

13. The method of claim 1, further comprising calcining the nickel starting material prior to the contacting with the reductant.

14. The method of claim 1, further comprising precipitating the nickel starting material prior to the contacting with the reductant.

15. The method of claim 1, further comprising contacting the nickel starting material with steam during the contacting with the reductant.

16. The method of claim 1, further comprising rotating or turning the nickel starting material during the contacting with the reductant.

17. The method of claim 1, further comprising forming a complex between nickel atoms of the nickel-containing complexation precursor and one or more phosphorus-containing ligands.

18. A nickel-containing complexation precursor comprising about 1,500 ppmw to about 500,000 ppmw amorphous nickel sulfide ($NiS_x$).

19. A method for making a complex comprising nickel and a phosphorus-containing ligand, said method comprising contacting nickel metal containing from 1,500 ppmw to 500,000 ppmw as amorphous nickel sulfide ($NiS_x$) with Ligand (V):

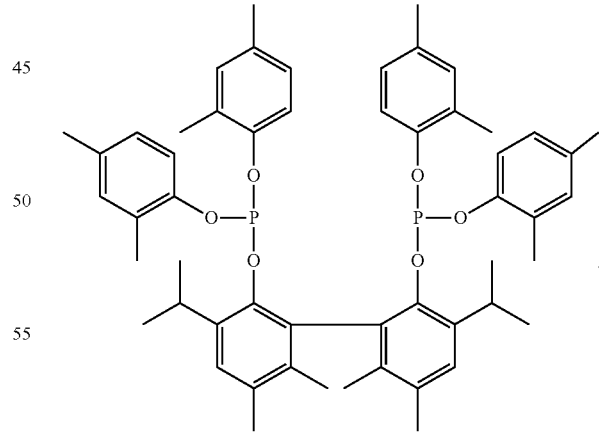

* * * * *